US010414729B2

(12) United States Patent
Smirnov et al.

(10) Patent No.: US 10,414,729 B2
(45) Date of Patent: Sep. 17, 2019

(54) SITE-SPECIFIC DYNAMIC NUCLEAR POLARIZATION NMR AGENTS

(71) Applicant: North Carolina State University, Raleigh, NC (US)

(72) Inventors: Alexej I. Smirnov, Raleigh, NC (US); Maxim Anatolyevich Voynov, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 323 days.

(21) Appl. No.: 15/222,428

(22) Filed: Jul. 28, 2016

(65) Prior Publication Data
US 2017/0029377 A1    Feb. 2, 2017

Related U.S. Application Data

(60) Provisional application No. 62/197,732, filed on Jul. 28, 2015.

(51) Int. Cl.
*C07D 211/94* (2006.01)
*C07D 211/56* (2006.01)
*G01N 24/12* (2006.01)
*G01R 33/62* (2006.01)

(52) U.S. Cl.
CPC .......... *C07D 211/94* (2013.01); *G01N 24/12* (2013.01); *G01R 33/62* (2013.01)

(58) Field of Classification Search
CPC ..................... C07D 211/56; C07D 211/94
See application file for complete search history.

(56) References Cited

U.S. PATENT DOCUMENTS

| 2003/0166160 A1* | 9/2003 | Hawley | C07K 14/70503 435/69.7 |
|---|---|---|---|
| 2012/0226022 A1* | 9/2012 | Kozlowski | A61K 47/48215 530/350 |

OTHER PUBLICATIONS

Claire Sauvee et al. Highly Efficient, Water-Soluble Polarizing Agents for Dynamic Nuclear Polarization at High Frequency, Angew. Chem. Int. Ed, 52, 10858-10861. (Year: 2013).*
Maly, T.; Cui, D.; Griffin, R. G.; Miller, A. F. 1H Dynamic Nuclear Polarization Based on an Endogenous Radical. J. Phys. Chem. B 2012, 116, 7055-7065.
Vitzthum, V.; Borcard, F.; Jannin, S.; Morin, M.; Mieville, P.; Caporini, M. A.; Sienkiewicz, A.; Gerber-Lemaire, S.; Bodenhausen, G. Fractional Spin-Labeling of Polymers for Enhancing NMR Sensitivity by Solvent-Free Dynamic Nuclear Polarization. ChemPhysChem 2011, 12, 2929-2932.
Wylie, B. J.; Dzikovski, B. G.; Pawsey, S.; Caporini, M.; Rosay, M.; Freed, J. H.; McDermott, A. E. Dynamic Nuclear Polarization of Membrane Proteins: Covalently Bound Spin-labels at Protein-Protein Interfaces. J. Biomol. NMR 2015, 61, 361-367.
Takahashi, H.; Ayala, I.; Bardet, M.; De Paepe, G.; Simorre, J. P.; Hediger, S. Solid-State NMR on Bacterial Cells: Selective Cell Wall Signal Enhancement and Resolution Improvement using Dynamic Nuclear Polarization. J. Am. Chem. Soc. 2013, 135, 5105-5110.
Smith, A. N.; Caporini, M. A.; Fanucci, G. E.; Long, J. R. A Method for Dynamic Nuclear Polarization Enhancement of Membrane Proteins. Angew. Chem., Int. Ed. 2015, 54, 1542-1546.
Fernandez-de-Alba, C.; Takahashi, H.; Richard, A.; Chenavier, Y.; Dubois, L.; Maurel, V.; Lee, D.; Hediger, S.; De Paepe, G. Matrix-Free DNP-Enhanced NMR Spectroscopy of Liposomes Using a Lipid-Anchored Biradical. Chem.—Eur. J. 2015, 21, 4512-4517.
Wang, S.; Munro, R. A.; Shi, L.; Kawamura, I.; Okitsu, T.; Wada, A.; Kim, S. Y.; Jung, K. H.; Brown, L. S.; Ladizhansky, V. Solid-state NMR spectroscopy Structure Determination of a Lipid-Embedded Heptahelical Membrane Protein. Nat. Methods 2013, 10, 1007-1012.
Shi, L.; Kawamura, I.; Jung, K. H.; Brown, L. S.; Ladizhansky, V. Conformation of a Seven-Helical Transmembrane Photosensor in the Lipid Environment. Angew. Chem., Int. Ed. 2011, 50, 1302-1305.
Wang, S.; Munro, R. A.; Kim, S. Y.; Jung, K. H.; Brown, L. S.; Ladizhansky, V. Paramagnetic Relaxation Enhancement Reveals Oligomerization Interface of a Membrane Protein. J. Am. Chem. Soc. 2012, 134, 16995-16998.
Rosen, G. M. Use of Sodium Cyanoborohydride in Preparation of Biologically-Active Nitroxides. J. Med. Chem. 1974, 17, 358-360.
Luckhurst, G. R.: In Spin Labeling: Theory and Applications; Berliner, L. J., Ed.; Academic Press: New York, 1976; pp. 133-181.

(Continued)

*Primary Examiner* — Michael G. Hartley
*Assistant Examiner* — Jagadishwar R Samala
(74) *Attorney, Agent, or Firm* — Thomas | Horstemeyer, LLP

(57) ABSTRACT

Dynamic nuclear polarization (DNP) agents are provided for DNP nuclear magnetic resonance of analytes. The DNP agents can have the structure A-X-L-R, where A is none or an amphiphilic group; X is a coupling group capable of site-specific binding with the analyte or, when A is an amphiphilic group, capable of site-specific binding with the amphiphilic group; L is a bond or a linker group; and R is a poly-radical group. The poly-radical can be a di-radical, a tri-radical, a tetra-radical, or a combination thereof. Methods of NMR measurement of an analyte comprising an NMR-detectable nucleus are provided. The methods can include the steps of providing a frozen sample containing the analyte and a DNP agent; applying radiation having a frequency that excites electron spin transitions in the DNP agent at an intensity to polarize the NMR-detectable nucleus; and detecting a signal from nuclear spin transitions in the NMR-detectable nucleus.

23 Claims, 7 Drawing Sheets

(56) References Cited

OTHER PUBLICATIONS

Luckhurst, G. R.; Pedulli, G. F. Interpretation of Biradical Electron Resonance Spectra. J. Am. Chem. Soc. 1970, 92, 4738-4739.
Kondoh, M.; Inoue, K.; Sasaki, J.; Spudich, J. L.; Terazima, M. Transient Dissociation of the Transducer Protein from Anabaena Sensory Rhodopsin Concomitant with Formation of the M State Produced upon Photoactivation. J. Am. Chem. Soc. 2011, 133, 13406-13412.
Hustedt, E. J.; Stein, R. A.; Sethaphong, L.; Brandon, S.; Zhou, Z.; DeSensi, S. C. Dipolar Coupling Between Nitroxide Spin Labels: The Development and Application of a Tether-In-A-Cone Model. Biophys. J. 2006, 90, 340-356.
Beit-Yannai, E.; Zhang, R.; Trembovler, V.; Samuni, A.; Shohami, E. Cerebroprotective Effect of Stable Nitroxide Radicals in Closed Head Injury in the Rat. Brain Res. 1996, 717, 22-28.
Zhang, R.; Hirsch, O.; Mohsen, M.; Samuni, A. Effects of Nitroxide Stable Radicals on Juglone Cytotoxicity. Arch. Biochem. Biophys. 1994, 312, 385-391. 918 (53) Jeschke, G. DEER Distance Measurements on Proteins. Annu. Rev. Phys. Chem. 2012, 63, 419-446.
Jeschke, G. Determination of the Nanostructure of Polymer Materials by Electron Paramagnetic Resonance Spectroscopy. Macromol. Rapid Commun. 2002, 23, 227-246.
Fafarman, A. T.; Borbat, P. P.; Freed, J. H.; Kirshenbaum, K. Characterizing the Structure and Dynamics of Folded Oligomers: Pulsed ESR Studies of Peptoid Helices. Chem. Commun. 2007, 377-379
Milov, A. D.; Naumov, B. D.; Tsvetkov, Y. D. The Effect of Microwave Pulse Duration on the Distance Distribution Function between Spin Labels Obtained by PELDOR Data Analysis. Appl. Magn. Reson. 2004, 26, 587-599.
Milikisyants, S.; Scarpelli, F.; Finiguerra, M. G.; Ubbink, M.;Huber, M. A Pulsed EPR Method to Determine Distances between Paramagnetic Centers with Strong Spectral Anisotropy and Radicals: The Dead-Time Free RIDME Sequence. J. Magn. Reson. 2009, 201, 48-56.
Jeschke, G.; Chechik, V.; Ionita, P.; Godt, A.; Zimmermann, H.; Banham, J.; Timmel, C. R.; Hilger, D.; Jung, H. DeerAnalysis2006—a Comprehensive Software Package for Analyzing Pulsed ELDOR Data. Appl. Magn. Reson. 2006, 30, 473-498.
Hu, K. N.; Song, C.; Yu, H. H.; Swager, T. M.; Griffin, R. G. High-frequency Dynamic Nuclear Polarization using Biradicals: A Multifrequency EPR Lineshape Analysis. J. Chem. Phys. 2008, 128, 052302.
Ward, M. E.; Wang, S.; Munro, R. A.; Ritz, E.; Hung, I; Gor'kov, P. L.; Jiang, Y.; Liang, H.; Brown, L. S.; Ladizhansky, V. In situ Structural Studies of Anabaena Sensory Rhodopsin in the E. coli Membrane. Biophys. J. 2015, 108, 1683-1696.
Thurber, K. R.; Tycko, R. Perturbation of Nuclear Spin Polarizations in Solid State NMR of Nitroxide-Doped Samples by Magic-Angle Spinning without Microwaves. J. Chem. Phys. 2014, 140, 184201.
Corzilius, B.; Andreas, L. B.; Smith, A. A.; Ni, Q. Z.; Griffin, R. G. Paramagnet Induced Signal Quenching in MAS-DNP Experiments in Frozen Homogeneous Solutions. J. Magn. Reson. 2014, 240, 113-123.
Henderson, R.; Unwin, P. N. Three-dimensional Model of Purple Membrane Obtained by Electron Microscopy. Nature 1975, 257, 28-32.
Barnes, A. B.; Corzilius, B.; Mak-Jurkauskas, M. L.; Andreas, L. B.; Bajaj, V. S.; Matsuki, Y.; Belenky, M. L.; Lugtenburg, J.; Sirigiri, J. R.; Temkin, R. J.; et al. Resolution and Polarization Distribution in Cryogenic DNP/MAS Experiments. Phys. Chem. Chem. Phys. 2010, 12, 5861-5867.
Akbey, U.; Franks, W. T.; Linden, A.; Lange, S.; Griffin, R. G.; van Rossum, B. J.; Oschkinat, H. Dynamic Nuclear Polarization of Deuterated Proteins. Angew. Chem., Int. Ed. 2010, 49, 7803-7806.

Lee, M.; Hong, M. Cryoprotection of Lipid Membranes for High-Resolution Solid-State NMR Studies of Membrane Peptides and Proteins at Low Temperature. J. Biomol. NMR 2014, 59, 263-277. Website: www.easyspin.org.
Yau et al. "Synthesis and evaluation of nitroxide-based oligoradicals for low-temperature dynamic nuclear polarization in solid" Journal of Magnetic Resonance 244 (May 2014) pp. 98-106.
Smith et al. "A Method for Dynamic Nuclear Polarization Enhancement of Membrane Proteins" Angew. Chem. Int. Ed. (2015) pp. 1542-1546.
Matsuki et al. "Dynamic Nuclear Polarization with a Rigid Biradical" Angew. Chem. Int. Ed. (2009) 48, pp. 4996-5000 DOI: 10.1002/anie.200805940.
Thurber et al. "Low-temperature dynamic nuclear polarization at 9.4 T with a 30 mW Microwave source" Journal of Magnetic Resonance 204 (2010) 303-313 DOI:10.1016/j.jmr.2010.03.016.
Dane et al. "Rigid Orthogonal Bis-TEMPO Biradicals with Improved Solubility for Dynamic Nuclear Polarization" The Journal of Organic Chemistry (Feb. 2012) pp. 1789-1797.
Smith et al. "A Method for Dynamic Nuclear Polarization Enhancement of Membrane Proteins" Angew. Chem. Int. Ed. (2015) 54, 1542-1546.
Zagdoun et al. "A Slowly Relaxing Rigid Biradical for Efficient Dynamic Nuclear Polarization Surface-Enhanced NMR Spectroscopy: Expeditious Characterization of Functional Group Manipulation in Hybrid Materials" J. Am. Chem.Soc. (2012) 134, 2284-2291.
Zagdoun et al. "Large Molecular Weight Nitroxide Biradicals Providing Efficient Dynamic Nuclear Polarization at Temperatures up to 200 K" J. Am. Chem. Soc. (2013) 135, 12790-12797.
Fielding et al. "New Developments in Spin Labels for Pulsed Dipolar EPR" Molecules 2014, 19, 16998-17025; DOI: 10.3390/molecules191016998.
M.M. Rosay (2001). Sensitivity-Enhanced Nuclear Magnetic Resonance of Biological Solids. Massachusetts Institute of Technology, Cambridge, MA.
Fung, B. M.; Khitrin, A. K.; Ermolaev, K.: An Improved Broadband Decoupling Sequence for Liquid Crystals and Solids. J Magn Reson 2000, 142, 97-101.
Savitsky, A.; Dubinskii, A. A.; Flores, M.; Lubitz, W.; Mobius, K. Orientation-resolving Pulsed Electron Dipolar High-Field EPR Spectroscopy on Disordered Solids: I. Structure of Spin-Correlated Radical Pairs in Bacterial Photosynthetic Reaction Centers. J. Phys.Chem. B 2007, 111, 6245-6262.
Jaroniec, C. P. Solid-state Nuclear Magnetic Resonance Structural Studies of Proteins using Paramagnetic probes. Solid State Nucl. Magn. Reson. 2012, 43-44, 1-13.
Song, C. S.; Hu, K. N.; Joo, C. G.; Swager, T. M.; Griffin, R. G: Totapol: A Biradical Polarizing Agent for Dynamic Nuclear Polarization Experiments in Aqueous Media. J Am Chem Soc 2006, 128, 11385-11390.
Shaked, Z.; Szajewski, R. P.; Whitesides, G. M.: Rates of Thiol-Disulfide Interchange Reactions Involving Proteins and Kinetic Measurements of Thiol pKa Values. Biochemistry 1980, 19, 4156-4166.
Shi, L; Kawamura, I.; Jung, K. H.; Brown, L. S.; Ladizhansky, V.: Conformation of a Seven-Helical Transmembrane Photosensor in the Lipid Environment. Angew Chem Int Ed Engl 2011, 50, 1302-1305.
Wada, Y.; Kawanabe, A.; Furutani, Y.; Kandori, H.; Ohtani, H: Quantum Yields for the Light Adaptations in Anabaena Sensory Rhodopsin and Bacteriorhodopsin. Chem Phys Lett 2008, 453, 105-108.
Religa, T. L.; Ruschak, A. M.; Rosenzweig, R.; Kay, L. E.: Site-directed Methyl Group Labeling as an NMR Probe of Structure and Dynamics in Supramolecular Protein Systems: Applications to the Proteasome and to the Clpp Protease. J Am Chem Soc 2011, 133, 9063-9068.
Ward, M. E; Wang, S.; Krishnamurthy, S.; Hutchins, H.; Fey, M.; Brown, L. S.; Ladizhansky, V.: High-resolution Paramagnetically Enhanced Solid-State NMR Spectroscopy of Membrane Proteins at Fast Magic Angle Spinning. J Biomol NMR 2014, 58, 37-47.
DaCosta, C. J.; Baenziger, J. E: A Rapid Method for Assessing Lipid:Protein and Detergent:Protein Ratios in Membrane-Protein Crystallization. Acta Crystallogr D Biol Crystallogr 2003, 59, 77-83.

(56) References Cited

OTHER PUBLICATIONS

Thurber, K. R.; Tycko, R.: Measurement of Sample Temperatures Under Magic-Angle Spinning from the Chemical Shift and Spin-Lattice Relaxation Rate of Br-79 in KBr Powder. J Magn Reson 2009, 196, 84-87.
Hartmann, S. R.; Hahn, E. L.: Nuclear Double Resonance in the Rotating Frame Phys Rev 1962, 128, 2042-2053.
Mak-Jurkauskas, M. L.; Bajaj, V. S.; Hornstein, M. K.; Belenky, 725 M.; Griffin, R. G.; Herzfeld, J. Energy Transformations Early in the Bacteriorhodopsin Photocycle Revealed by DNP-Enhanced Solid-state 726 NMR. Proc. Natl. Acad. Sci. U. S. A. 2008, 105, 883-888.
Bajaj, V. S.; Mak-Jurkauskas, M. L.; Belenky, M.; Herzfeld, J.; 728 Griffin, R. G. Functional and Shunt States of Bacteriorhodopsin 729 Resolved by 250 GHz Dynamic Nuclear olarization-enhanced Solid-730 state NMR. Proc. Natl. Acad. Sci. U. S. A. 2009, 106, 9244-9249.
Renault, M.; Pawsey, S.; Bos, M. P.; Koers, E. J.; Nand, D.; 732 Tommassen-van Boxtel, R.; Rosay, M.; Tommassen, J.; Maas, W. E.; 733 Baldus, M. Solid-state NMR Spectroscopy on Cellular Preparations 734 Enhanced by Dynamic Nuclear Polarization. Angew. Chem., Int. Ed. 735 2012, 51, 2998-3001.
Ong, Y. S.; Lakatos, A.; Becker-Baldus, J.; Pos, K. M.; Glaubitz, C. 737 Detecting Substrates Bound to the Secondary Multidrug Efflux Pump 738 EmrE by DNP-enhanced Solid-state NMR. J. Am. Chem. Soc. 2013, 739 135, 15754-15762.
Debelouchina, G. T.; Bayro, M. J.; Fitzpatrick, A. W.; 741 Ladizhansky, V.; Colvin, M. T.; Caporini, M. A.; Jaroniec, C. P.; 742 Bajaj, V. S.; Rosay, M. Macphee, et al: Higher Order Amyloid Fibril Structure by MAS NMR and DNP Spectroscopy. J. Am. Chem. Soc. 2013, 135, 19237-19247.
Fricke, P.; Demers, J. P.; Becker, S.; Lange, A. Studies on the 746 MxiH Protein in T3SS Needles Using DNP-enhanced ssNMR Spectroscopy. ChemPhysChem 2014, 15, 57-60.
Kaplan, M.; Cukkemane, A.; van Zundert, G. C. P.; Narasimhan, 749 S.; Daniels, M.; Mance, D.; Waksman, G.; Bonvin, A. M. J. J.; Fronzes, 750 R. Folkers, et al.: Probing a Cell-Embedded Megadalton Protein Complex by DNP-supported solid-state NMR. Nat. Methods 2015, 12, 752 649-653.
Ardenkjaer-Larsen, J. H.; Fridlund, B.; Gram, A.; Hansson, G.; 754 Hansson, L.; Lerche, M. H.; Servin, R.; Thaning, M.; Golman, K. Increase in Signal-to-noise Ratio of > 10,000 Times in Liquid-state 756 NMR. Proc. Natl. Acad. Sci. U. S. A. 2003, 100, 10158-10163.
Golman, K.; in 't Zandt, R.; Thaning, M. Real-time Metabolic Imaging. Proc. Natl. Acad. Sci. U. S. A. 2006, 103, 11270 -11275.
Wilson, D. M.; Hurd, R. E.; Keshari, K.; Van Criekinge, M.; 760 Chen, A. P.; Nelson, S. J.; Vigneron, D. B.; Kurhanewicz, J. Generation of Hyperpolarized Substrates by Secondary Labeling with [1,1-13C] Acetic Anhydride. Proc. Natl. Acad. Sci. U. S. A. 2009, 106, 5503-5507.
Ross, B. D.; Bhattacharya, P.; Wagner, S.; Tran, T.; Sailasuta, N. 764 Hyperpolarized MR Imaging: Neurologic Applications of Hyperpolarized Metabolism. AJNR Am. J. Neuroradiol 2010, 31, 24-33.
Lesage, A; Lelli, M.; Gajan, D.; Caporini, M. A.; Vitzthum, V.; 767 Mieville, P.; Alauzun, J.; Roussey, A; Thieuleux, C.; Mehdi, A.; et al. Surface Enhanced NMR Spectroscopy by Dynamic Nuclear Polarization. J. Am. Chem. Soc. 2010, 132, 15459-15461.
Lelli, M.; Gajan, D.; Lesage, A.; Caporini, M. A.; Vitzthum, V.; Mieville, P.; Heroguel, F.; Rascon, F.; Roussey, A.; Thieuleux, C.; et al.Fast Characterization of Functionalized Silica Materials by Silicon-29 Surface-enhanced NMR Spectroscopy Using Dynamic Nuclear Polarization. J. Am. Chem. Soc. 2011, 133, 2104-2107.
Rossini, A. J.; Zagdoun, A.; Lelli, M.; Lesage, A.; Coperet, C.; Emsley, L. Dynamic Nuclear Polarization Surface Enhanced NMR Spectroscopy. Acc. Chem. Res. 2013, 46, 1942-1951.
Takahashi, H.; Viverge, B.; Lee, D.; Rannou, P.; De Paepe, G. Towards Structure Determination of Self-Assembled Peptides Using Dynamic Nuclear Polarization Enhanced Solid-State NMR Spectroscopy. Angew. Chem., Int. Ed. 2013, 52, 6979-6982.
Overhauser, A. W. Polarization of Nuclei in Metals. Phys. Rev.1953, 92, 411-415.

Carver, T. R.; Slichter, C. P. Polarization of Nuclear Spins in Metals. Phys. Rev. 1953, 92, 212-213.
Wind, R. A.; Duijvestijn, M. J.; Vanderlugt, C.; Manenschijn, A.;Vriend, J. Applications of Dynamic Nuclear-Polarization in C-13 Nmr Solids. Prog. Nucl. Magn. Reson. Spectrosc. 1985, 17, 33-67.
Maresch, G. G.; Kendrick, R. D.; Yannoni, C. S.; Galvin, M. E. Dynamic Nuclear-Polarization Via Confined Electrons in Bulk Solids. J. Magn. Reson. 1989, 82, 41-50.
Hall, D. A; Maus, D. C.; Geffen, G. J.; Inati, S. J.; Becerra, L. R.; Dahlquist, F. W.; Griffin, R. G. Polarization-enhanced NMR Spectroscopy of Biomolecules in Frozen Solution. Science 1997, 276, 930-932.
Hwang, C. F.; Hill, D. A. New Effect in Dynamic Polarization. Phys. Rev. Lett. 1967, 18, 110-112.
Hu, K. N.; Debelouchina, G. T.; Smith, A. A.; Griffin, R. G. Quantum Mechanical Theory of Dynamic Nuclear Polarization in 801 Solid Dielectrics. J. Chem. Phys. 2011, 134, 125105.
Hu, K. N.; Yu, H. H.; Swager, T. M.; Griffin, R. G. Dynamic Nuclear Polarization With Biradicals. J. Am. Chem. Soc. 2004, 126, 10844-10845.
Matsuki, Y.; Maly, T.; Ouari, O.; Karoui, H.; Le Moigne, F.; Rizzato, E.; Lyubenova, S.; Herzfeld, J.; Prisner, T.; Tordo, P.; et al. Dynamic Nuclear Polarization with a Rigid Biradical. Angew. Chem., Int. Ed. 2009, 48, 4996-5000.
Thurber K. R.; Yau W. M.; Tycko, R. Low-temperature Dynamic Nuclear Polarization at 9.A T with a 30 mW Microwave Source. J. Magn. Reson. 2010, 204, 303-313.
Dane, E. L.; Corzilius, B.; Rizzato, E.; Stocker, P.; Maly, T.;Smith, A. A.; Griffin, R. G.; Ouari, O.; Tordo, P.; Swager, T. M. Rigid Orthogonal Bis-TEMPO Biradicals with Improved Solubility for Dynamic Nuclear Polarization. J. Org. Chem. 2012, 77, 1789-1797.
Sauvee, C.; Rosay, M.; Casano, G.; Aussenac, F.; Weber, R. T.; Ouari, O.; Tordo, P. Highly Efficient, Water-Soluble Polarizing Agents for Dynamic Nuclear Polarization at High Frequency. Angew. Chem., lnt. Ed. 2013, 52, 10858-10861.
Kiesewetter, M. K.; Corzilius, B.; Smith, A. A.; Griffin, R. G.; Swager, T. M. Dynamic Nuclear Polarization with a Water-Soluble Rigid Biradical. J. Am. Chem. Soc. 2012, 134, 4537-4540.
Zagdoun, A.; Casano, G.; Ouari, O.; Lapadula, G.; Rossini, A. J.; Lelli, M.; Baffert, M.; Gajan, D.; Veyre, L.; Maas; et al. A Slowly Relaxing Rigid Biradical for Efficient Dynamic Nuclear Polarization Surface-enhanced NMR Spectroscopy: Expeditious Characterization of Functional Group Manipulation in Hybrid Materials. J. Am. Chem. Soc. 2012, 134, 2284-2291.
Zagdoun, A.; Casano, G.; Ouari, O.; Schwarzwalder, M.; Rossini, A. J.; Aussenac, F.; Yulikov, M.; Jeschke, G.; Coperet, C. Lesage, et al.: Large Molecular Weight Nitroxide Biradicals Providing Efficient Dynamic Nuclear Polarization at Temperatures up to 200 K. J. Am. Chem. Soc. 2013, 135, 12790-12797.
Yau, W. M.; Thurber, K. R.; Tycko, R. Synthesis and Evaluation of Nitroxide-Based Oligoradicals for Low-Temperature Dynamic Nuclear Polarization in Solid State NMR. J. Magn. Reson. 2014, 244, 98-106. 841.
Koers, E. J.; van der Cruijsen, E. A.; Rosay, M.; Weingarth, M.; Prokofyev, A.; Sauvee, C.; Ouari, O.; van der Zwan, J.; Pongs, O.; Tordo, P.; et al. NMR-based Structural Biology Enhanced by Dynamic Nuclear Polarization at High Magnetic Field. J. Biomol. NMR 2014, 60, 157-168.
Rossini, A. J.; Zagdoun, A.; Lelli, M.; Gajan, D.; Rascon, F.; Rosay, M.; Maas, W. E.; Coperet, C.; Lesage, A.; Emsley, L. One Hundred Fold Overall Sensitivity Enhancements for Silicon-29 NMR Spectroscopy of Surfaces by Dynamic Nuclear Polarization with CPMG Acquisition. Chemical Science 2012, 3, 108-115.
Takahashi, H.; Lee, D.; Dubois, L.; Bardet, M.; Hediger, S.; De Paepe, G. Rapid Natural-abundance 2D 13C-13C Correlation Spectroscopy Using Dynamic Nuclear Polarization Enhanced Solid-state NMR and Matrix-free Sample Preparation. Angew. Chem., Int. Ed. 855 2012, 51, 11766-11769.
Gajan, D.; Schwarzwalder, M.; Conley, M. P.; Gruning, W. R.; Rossini, A. J.; Zagdoun, A.; Lelli, M.; Yulikov, M.; Jeschke, G.; Sauvee, C.; et al. Solid-phase Polarization Matrixes for Dynamic

(56) References Cited

OTHER PUBLICATIONS

Nuclear Polarization from Homogeneously Distributed Radicals in Mesostructured Hybrid Silica Materials. J. Am. Chem. Soc. 2013, 135, 15459-15466.

* cited by examiner

SITE-SPECIFIC DYNAMIC NUCLEAR POLARIZATION NMR AGENTS

CROSS-REFERENCE TO RELATED APPLICATIONS

This application claims priority to, and the benefit of, U.S. provisional application entitled "SITE-SPECIFIC DYNAMIC NUCLEAR POLARIZATION NMR AGENTS" having Ser. No. 62/197,732, filed Jul. 28, 2015, the contents of which are incorporated by reference in their entirety.

STATEMENT OF GOVERNMENT SUPPORT

This invention was made with government support under Award Number DE-FG02-02ER15354 awarded by The Department of Energy. The government has certain rights in the invention.

BACKGROUND

Nuclear Magnetic Resonance (NMR) is one of the key methods for the determination of molecular structure. This method relies on detecting magnetization resulting from a Boltzmann population difference between the energy levels of nuclear spins that are split by the Zeeman and other magnetic interactions. Under currently attainable magnetic fields of up to ca. 15-23 T and typical temperatures of 100-300 K for NMR experiments, the nuclear spin population difference is small, thus limiting the magnitude of the NMR signal and the range of molecular systems that can be studied by this method. The nuclear spin polarization can be enhanced by up to several orders of magnitude by transferring an intrinsically larger polarization from a magnetically coupled electronic spin system. Such a transfer is achieved by the Dynamic Nuclear Polarization (DNP) method, with applications in the areas of magnetic resonance-based protein structure determination,[1-7] imaging,[8-11] and materials and surface science.[12-15]

In a typical DNP NMR experiment, electromagnetic radiation of the micrometer to millimeter wave length (mm-wave) is applied to saturate the electronic spin transitions of paramagnetic agents that are typically added to the system.[16-20] The 660-fold higher polarization of the electronic spins is then partially transferred to the nuclear spins, resulting in a hyperpolarized state for the latter. While the initial high field DNP-NMR studies employed a stable monoradical nitroxide, TEMPO (2,2,6,6-Tetramethyl-1-piperidinyloxy), as a polarizing agent,[20] it was later recognized that the use of biradicals facilitates spin polarization transfer at 80-120 K via cross effect mechanism[21,22] yielding a greater polarization of the nuclear spins and, thus, an increase in NMR signal. Following the pioneering work by Hu et al. who have tethered a pair of TEMPO monoradicals with a polyethylene glycol linker,[23] many bi- or higher order radicals of different geometries and solubility have been synthesized and tested for DNP.[24-32] For example, significant improvements in DNP enhancement have been demonstrated by using bTbK[25] and its derivatives[27,29] that contain two rigidly linked TEMPO fragments to achieve approximate orthogonality of the electronic g-tensors. Recently, bis-cyclohexyl-TEMPO-bisketal (bCTbK) and a higher molecular weight TEKPoL have been shown to retain the DNP enhancement at higher temperatures.[31] Two biradicals, TOTAPOL[24] and AMUPol[28] offer the best compromise between the magnitude of the DNP enhancement and solubility, and are now widely employed in the magic angle spinning (MAS) DNP-NMR of proteins,[1-6,33] including a recent example of in situ study of the bacterial type IV secretion system core complex.[7]

While the magnitude of the DNP enhancement is one of the most important factors contributing to the absolute sensitivity of DNP-NMR measurements, many authors have pointed out to the significance of other parameters that may limit the total gain in the signal intensity.[34,35] One factor is related to the necessity of achieving a homogeneous distribution of the polarizing agents that are exogenously added to a typically diamagnetic sample. Since all but a very few DNP experiments with protein samples are carried out in aqueous solutions and at below-freezing temperatures, a glass-forming solvent such as glycerol must be added to achieve a homogeneous distribution of the polarizing agents and prevent the formation of ice crystals, that is, to form a so-called glassy matrix.[36] The necessity to use some large amounts of glycerol (10-20 mM concentration) effectively reduces the amount of protein in such a sample. For example, in the experiments with TOTAPOL described below, the incorporation of 60% glycerol leads to an approximately fourfold decrease in the maximally attainable protein concentration due to inefficient pelleting, thus, proportionally reducing the effective filling factor and the resultant NMR signal.

A number of alternative "matrix-free" sample preparation approaches have been described in the literature. In the first demonstration of DNP from covalently attached radicals, Miller, Griffin and co-workers have employed an endogenously present stable flavin mononucleotide radical, semiquinone, to enhance the NMR signal of flavodoxin.[37] Bodenhausen et al. have covalently attached TOTAPOL to the C-terminal amino acid of a decapeptide through the ester bond.[38] McDermott et al. reported on DNP enhancement from a "pseudo-biradical" formed upon the dimerization of gramicidin labeled by monoradicals at the dimer interface.[39] De Paëpe et al. have taken advantage of the high partitioning of TOTAPOL within microcrystalline cellulose[35] as well as its strong binding affinity to cell wall polymers (peptidoglycan)[40] to obtain DNP-enhanced NMR spectra of the biopolymers constituting plant cell walls. DNP of phospholipid-embedded peptides from a mixture of two different monoradical-labeled lipids has been demonstrated by Long et al.,[41] while, De Paëpe and collaborators have demonstrated the DNP of lipids in liposomes from a biradical functionalized with an acyl chain to provide for preferential partitioning into the lipid bilayer.[42]

There remains a need for new and improved agents for dynamic nuclear polarization NMR studies of a range of analytes.

SUMMARY

Dynamic Nuclear Polarization (DNP) enhances the signal in solid-state NMR of proteins by transferring polarization from electronic spins to the nuclear spins of interest. Typically, both the protein and an exogenous source of electronic spins, such as a biradical, are either co-dissolved or suspended and then frozen in a glycerol/water glassy matrix to achieve a homogeneous distribution. While the use of such a matrix protects the protein upon freezing, it also reduces the available sample volume (by ca. a factor of 4 in our experiments) and causes proportional NMR signal loss. Here we demonstrate an alternative approach that does not rely on dispersing the DNP agent in a glassy matrix. We synthesize a biradical, ToSMTSL, which is based on the known DNP agent TOTAPOL, but also contains a thiol-specific methanethiosulfonate group to allow for incorporating this biradical into a protein in a site-directed manner. ToSMTSL was characterized by EPR and tested for DNP of a heptahelical transmembrane protein, *Anabaena* Sensory Rhodopsin (ASR), by covalent modification of solvent-exposed cysteine residues in two $^{15}$N-labeled ASR mutants. DNP enhancements were measured at 400 MHz/263 GHz NMR/EPR frequencies for a series of samples prepared in deuterated and protonated buffers and with varied biradical/protein ratios. While the maximum DNP enhancement of 15 obtained in these samples is comparable to that observed for an ASR sample co-suspended with ~17 mM TOTAPOL in a $d_8$-glycero/$D_2O$/$H_2O$ matrix, the achievable sensitivity would be fourfold greater due to the gain in the filling factor. We anticipate that the DNP enhancements could be further improved by optimizing the biradical structure. The use of covalently attached biradicals would broaden the applicability of DNP NMR to structural studies of proteins.

In various embodiments, dynamic nuclear polarization (DNP) agent for DNP nuclear magnetic resonance of an analyte are provided. The DNP agent can have a structure A-X-L-R or X-L-R (i.e. where A is none), where A can be an amphiphilic group, where X can be a coupling group, where L can be a bond or a linker group, and where R can be a poly-radical group. In embodiments where A is none, the coupling group can be capable of site-specific binding with the analyte. In embodiments where A is an amphiphilic group, the coupling group can be capable of site-specific binding with the amphiphilic group.

Various poly-radicals can be used such as a di-radical, a tri-radical, a tetra-radical, and a combination thereof. In some aspects, the R group includes 2 or more radicals connected through a flexible or rigid linker, where each radical is independently a nitroxide radical, a triarylmethyl radical, or a combination of thereof. Each radical can be independently selected from

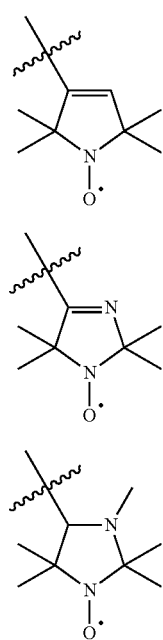

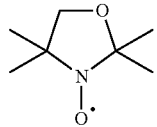

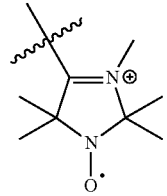

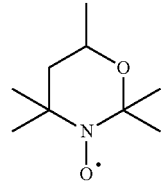

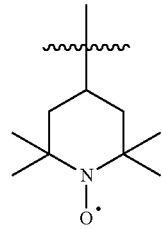

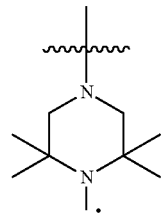

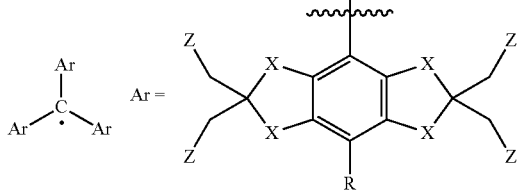

wherein each occurrence of X is independently $CH_2$, NH, O, or S; and wherein each occurrence of Z is independently H or a substituted or unsubstituted alkyl, heteroalkyl, alkenyl, or alkynyl group having from 1 to 30 carbon atoms.

In some embodiments, the R has the formula

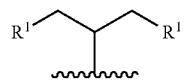

wherein each occurrence of $R^1$ is independently an —$X^1$-$L^1$-$M^1$; wherein each occurrence of $X^1$ is selected from the group consisting of —O—, —S—, or —N($R^2$)—, wherein $R^2$ selected from the group consisting of H, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms wherein each occurrence of $L^1$ is independently a bond or selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 12 carbon atoms; and wherein each occurrence of $M^1$ is independently a nitroxide radical or a triarylmethyl radical. In some aspects, each $M^1$ is independently selected for the group 1
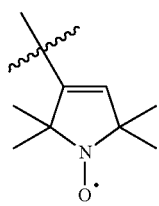

2
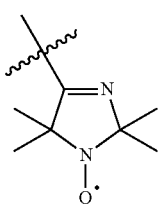

3
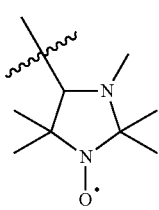

4
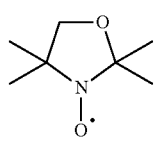

5
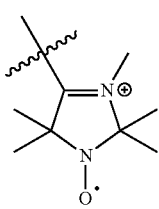

6
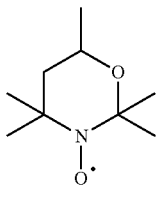

-continued

7
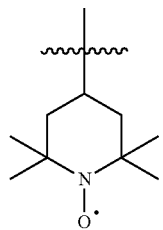

8
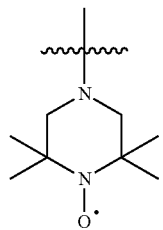

9
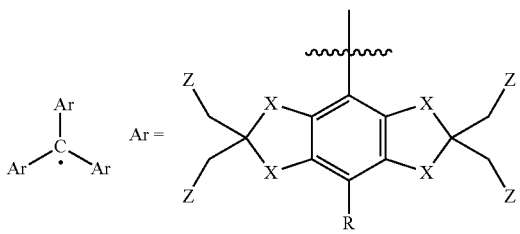

wherein each occurrence of X is independently $CH_2$, NH, O, or S; and wherein each occurrence of Z is independently H or a substituted or unsubstituted alkyl, heteroalkyl, alkenyl, or alkynyl group having from 1 to 30 carbon atoms.

In some embodiments, the DNP agent has a structure A-X-L-R or X-L-R (i.e. where A is none), where L is a bond or a linker group. In some aspects, the linker group is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 12 carbon atoms.

A variety of coupling groups can be used. In various aspects where A is none, the coupling group forms a covalent bond to the analyte. The coupling group can be an amine-reactive coupling group, an aldehyde-reactive coupling group, a sulfhydryl-reactive coupling group, or a combination thereof. In various aspects, the coupling group is a sulfhydryl-reactive coupling group selected from the group consisting of a maleimide group, a methanethiosulfonate group, a haloacetyl group, a pyridyl disulfide group, and a combination thereof.

The sulfhydryl-reactive coupling group can be a maleimide group having the structure

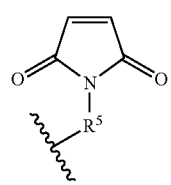

wherein $R^5$ is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms.

The sulfhydryl-reactive coupling group can be a methanethiosulfonate group having the structure

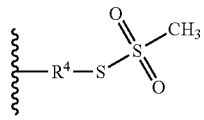

wherein R⁴ is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms.

The sulfhydryl-reactive coupling group can be a haloacetyl group having the structure

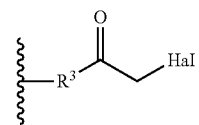

wherein R³ is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms; and wherein Hal is a halogen.

The sulfhydryl-reactive coupling group can be a pyridyl disulfide group having the structure

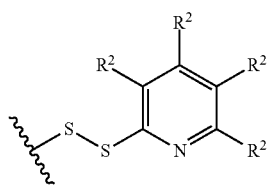

wherein each occurrence of R² is independently selected from the group consisting of hydrogen, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms or, when taken together with the atoms to which they are attached form a heterocycle having from 2 to 30 carbon atoms.

In various aspects, the reactive coupling group is a amine-reactive coupling group selected from the group consisting of an isothiocyanate, an isocyanate, an acyl azide, an NHS ester, a sulfonyl chloride, an aldehyde, an epoxide, an oxirane, a carbonate, an aryl halide, an imidoester, a carbodiimide, an anhydride, a fluorophenyl ester, and a combination thereof. In some aspects, the reactive coupling group is an aldehyde-reactive coupling group selected from the group consisting of a hydrazide, an alkoxyamine, a primary amine, and a combination thereof. In some aspects, the coupling group is a non-covalent coupling group that binds non-covalently to the analyte with a $K_d$ of $10^{-13}$ M to $10^{-16}$ M. In some aspects, the covalent coupling of DNP agent is achieved by click chemistry and in a combination with other coupling schemes. The non-covalent coupling group can be avidin, an avidin derivative, streptavidin, a streptavidin derivative, or a combination thereof.

A variety of analytes can be measured via NMR using the DNP agents provided herein. In some aspects, the analyte is an antibody and the coupling group is an antigen that binds specifically with the antibody. In some aspects, the analyte is a polynucleotide and the coupling group is an aptamer that binds specifically with an active site of the polynucleotide. Analytes can be proteins, nucleic acids, or combinations thereof. Various methods are provided for NMR measurement of an analyte comprising an NMR-detectable nucleus, the methods including providing a frozen sample containing the analyte and a DNP agent described herein; applying radiation having a frequency that excites electron spin transitions in the DNP agent at an intensity to polarize the NMR-detectable nucleus; and detecting a signal from nuclear spin transitions in the NMR-detectable nucleus. The DNP agent in presence of microwave excitation can provide for a significant enhancement in the NMR signal. In various aspects, the signal is greater than a second signal for the otherwise same NMR-detectable nucleus in the same analyte and taken under the same conditions except without the DNP agent in the sample and without microwave excitation. The NMR-detectable nucleus can include $^1H$, $^{13}C$, $^{15}N$, $^{19}F$, $^2Na$, and/or $^{31}P$. In various aspects, the NMR-detectable nucleus is a half-integer spin nucleus, e.g. having I of 1/2, 3/2, 5/2, etc.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
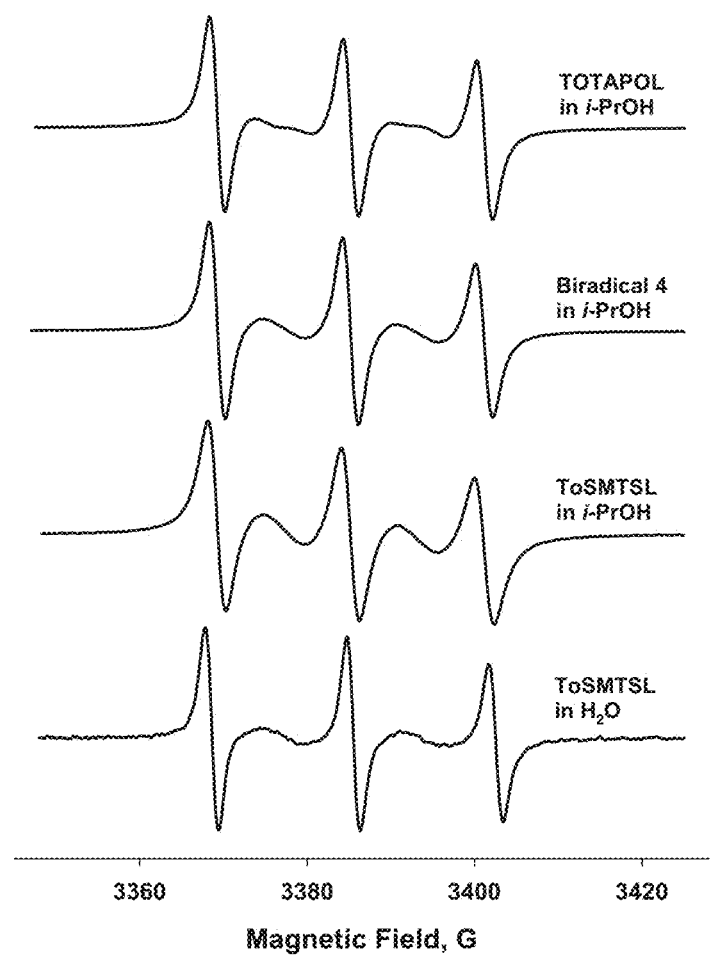
FIG. 1 is a graph of the room temperature X-band (9.5 GHz) continuous wave electron paramagnetic resonance (CW EPR) spectra of deoxygenated 1 mM isopropyl alcohol (i-PrOH) solutions of TOTAPOL 3, biradical 4 and ToSMTSL 6 and 0.1 mM aqueous solution of ToSMTSL 6.

Dynamic nuclear polarization (DNP) agents are provided useful for site-specific DNP nuclear magnetic resonance. The DNP agents overcome many of the aforementioned problems with standard approaches of DNP NMR that require the use of glassy solvent systems. The DNP agents have a poly-radical including a bi-radical or other higher radical and can bind, covalently or non-covalently, to the analyte in a site-specific manner. Methods of using the DNP agents are also provided. The methods can include the solution NMR, static and magic angle spinning (MAS) solid state NMR as well as magnetic resonance imaging (MRI) of a sample containing the analyte and the DNP agent. The DNP agents can result in a stronger NMR signal as compared to the otherwise same measurement except not using the DNP agent. Additional details and advantages will become apparent from the following discussion.

Here, we describe the synthesis of a nitroxide biradical label that, while being structurally similar to TOTAPOL, contains a methanethiosulfonate group (—SSO$_2$CH$_3$ or MTS). MTS can react selectively with the thiol group (—SH) of exposed cysteine residues to form a covalent attachment through the disulfide bond. Such a biradical, which we call ToSMTSL (Totapol Series MethaneThiosulfonate Spin Label), can be directly linked to a protein of interest, thereby providing a well-defined location of the polarized electronic spins with respect to the detectable nuclear spins. Furthermore, the use of covalently attached biradicals completely eliminates the stringent requirements for the glassy solvent system, offering a greater flexibility in the choosing of cryoprotectants; it also resolves the issues of limited solubility of some biradicals in aqueous solvents. We characterize the biradical by continuous wave (CW) EPR and double electron-electron resonance (DEER) spectroscopies at X-band (9.5 GHz), and then employ the biradical molecular tag for site-directed labeling of a heptahelical transmembrane protein *Anabaena* Sensory Rhodopsin (ASR) to demonstrate the biradical utility as a DNP polarizing agent. With knowledge of the full structure of a lipid-embedded ASR trimer[43] and of the exact location of the biradical with respect to the protein, we evaluate the effects and the distance range of paramagnetic quenching of the NMR signal by the electronic spins. Finally, we report the DNP enhancement factors for ASR samples with covalently attached biradical and compare those with the enhancements obtained for unmodified ASR with TOTAPOL dispersed in a glassy glycerol/water matrix.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'" includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The term "small molecule", as used herein, generally refers to an organic molecule that is less than 2000 g/mol in molecular weight, less than 1500 g/mol, less than 1000 g/mol, less than 800 g/mol, or less than 500 g/mol. Small molecules are non-polymeric and/or non-oligomeric.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties. "Amphiphilic material" as used herein refers to a material containing a hydrophobic or more hydrophobic oligomer or polymer (e.g., biodegradable oligomer or polymer) and a hydrophilic or more hydrophilic oligomer or polymer.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. Aryloxy can be represented by —O-aryl or O-heteroaryl, wherein aryl and heteroaryl are as defined below. The alkoxy and aryloxy groups can be substituted as described above for alkyl.

The terms "amine" and "amino" are art-recognized and refer to both unsubstituted and substituted amines, e.g., a moiety that can be represented by the general formula:

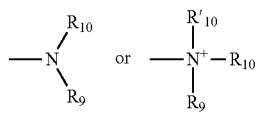

wherein $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

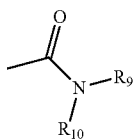

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —$CN$; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, and —CN.

The term "carbonyl" is art-recognized and includes such moieties as can be represented by the general formula:

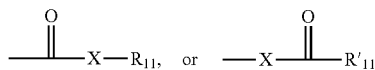

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valences of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, such as random, block, graft, etc. The copolymers can have any end-group, including capped or acid end groups.

The terms "polypeptide," "peptide" and "protein" generally refer to a polymer of amino acid residues. As used herein, the term also applies to amino acid polymers in which one or more amino acids are chemical analogues or modified derivatives of corresponding naturally-occurring amino acids. The term "protein", as generally used herein, refers to a polymer of amino acids linked to each other by peptide bonds to form a polypeptide for which the chain length is sufficient to produce tertiary and/or quaternary structure. The term "protein" excludes small peptides by definition, the small peptides lacking the requisite higher-order structure necessary to be considered a protein.

The terms "nucleic acid," "polynucleotide," and "oligonucleotide" are used interchangeably to refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general and unless otherwise specified, an analogue of a particular nucleotide has the same base-pairing specificity; i.e., an analogue of A will base-pair with T. The term "nucleic acid" is a term of art that refers to a string of at least two base-sugar-phosphate monomeric units. Nucleotides are the monomeric units of nucleic acid polymers. The term includes deoxyribonucleic acid (DNA) and ribonucleic acid (RNA) in the form of a messenger RNA, antisense, plasmid DNA, parts of a plasmid DNA or genetic material derived from a virus. Antisense is a polynucleotide that interferes with the function of DNA and/or RNA. The term nucleic acids refers to a string of at least two base-sugar-phosphate combinations. Natural nucleic acids have a phosphate backbone, artificial nucleic acids may contain other types of backbones, but contain the same bases. The term also includes PNAs (peptide nucleic acids), phosphorothioates, and other variants of the phosphate backbone of native nucleic acids.

A "functional fragment" of a protein, polypeptide or nucleic acid is a protein, polypeptide or nucleic acid whose sequence is not identical to the full-length protein, polypeptide or nucleic acid, yet retains at least one function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA binding function of a polypeptide can be determined, for example, by filter-binding, electrophoretic mobility shift, or immunoprecipitation assays. DNA cleavage can be assayed by gel electrophoresis. The ability of a protein to interact with another protein can be determined, for example, by co-immunoprecipitation, two-hybrid assays or complementation, e.g., genetic or biochemical. See, for example, Fields et al. (1989) *Nature* 340:245-246; U.S. Pat. No. 5,585,245 and PCT WO 98/44350.

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The term "site-specific", as used herein, refers to the specificity of an interaction for one or a few sites within a larger molecule. The sites may be individual functional groups such as a thiol or amine, individual nucleic acids or peptides, or even short sequences of about 2, 3, 4, 5, 6, 8, or 10 nucleic acids or peptides within a larger macromolecule. Site-specific can refer to binding of a coupling group where the coupling group have a binding affinity that is at least 10, 20, 50, or 100 times stronger for the site than for other sites.

Dynamic Nuclear Polarization Agents

Dynamic nuclear polarization (DNP) agents are provided. In some embodiments the DNP agents have the general formula X-L-R, where X is a coupling group capable of site-specific binding with an analyte, L is a bond or a linker group, and R is a poly-radical group. In some embodiments the DNP agents are providing having the general formula A-X-L-R where A is an amphiphilic group, X is a coupling group capable of site-specific binding with the amphiphilic group, and L and R are as defined above.

The DNP agent can have the following structure or a derivative thereof.

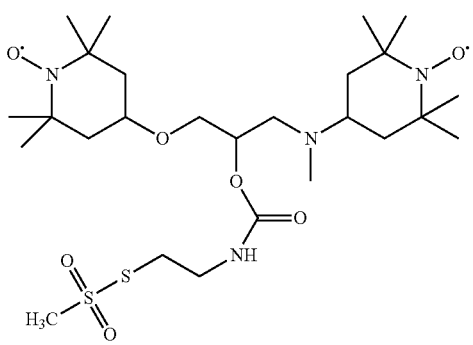

The DNP agent can have the following structure, or a derivative thereof

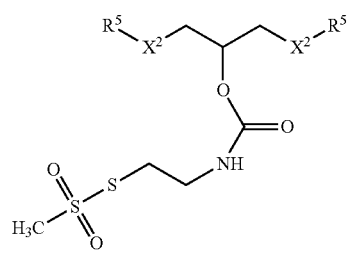

where each $X^2$ is independently —O—, —S—, or $N(R^6)$— wherein $R^6$ is independently hydrogen, halide, or a substituted or unsubstituted alkoxy, heteroalkoxy, alkyl, heteroalkyl, aryl, aryloxy, aralkyl, aralkyloxy, alkenyl, or alkynyl groups having from 1 to 30, 1 to 20, 1 to 12, or 1 to 6 carbon atoms; and where each occurrence of $R^5$ is independently a substituted or unsubstituted cyclic alkoxy, heteroalkoxy, alkyl, or heteroalkyl group having from 3 to 12, 3 to 10, 4 to 10, or 4 to 8 carbon atoms and having a nitroxide radical or a triarylmethyl radica group.

The DNP agent can have the following structure or a derivative thereof

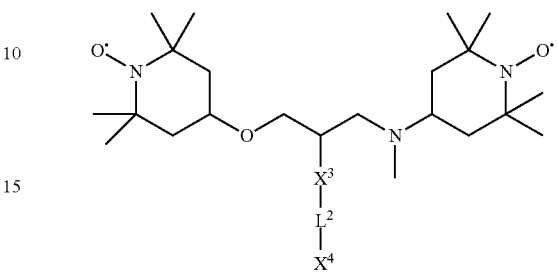

where $X^3$ is —O—, —S—, or $N(R^6)$— wherein $R^6$ is independently hydrogen, halide, or a substituted or unsubstituted alkoxy, heteroalkoxy, alkyl, heteroalkyl, aryl, aryloxy, aralkyl, aralkyloxy, alkenyl, or alkynyl groups having from 1 to 30, 1 to 20, 1 to 12, or 1 to 6 carbon atoms; where L2 is a substituted or unsubstituted alkoxy, heteroalkoxy, alkyl, heteroalkyl, aryl, aryloxy, aralkyl, aralkyloxy, alkenyl, or alkynyl groups having from 1 to 30, 1 to 20, 1 to 12, or 1 to 6 carbon atoms; and where X4 is a reactive coupling group such as a sulfhydryl reactive coupling group.

The DNP agent can include an amphiphilic group such as a phospholipid. For example, the DNP agent can have a structure according to the following formula

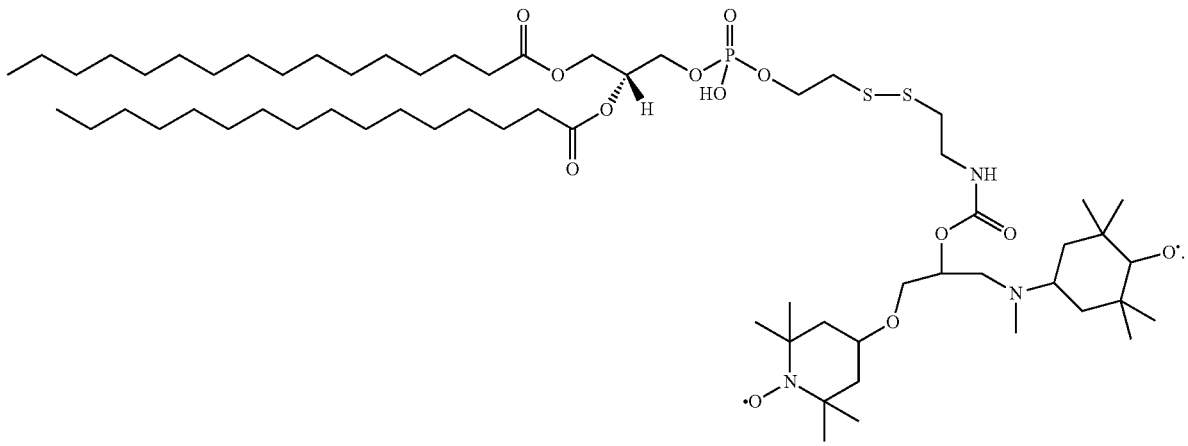

Coupling Groups

The DNP agent can include a coupling group capable of site-specific binding with the analyte. The DNP agent can include a coupling group capable of site-specific binding to an amphiphilic group such as a lipid or an amphiphilic polymer.

The site specific binding is, in some embodiments, covalent. In some examples the coupling group is capable of reacting with the analyte or with a site on the analyte to form a covalent bond. The reaction can be reversible. The coupling reaction may include the use of a catalyst, heat, pH buffers, light, or a combination thereof.

Examples of coupling groups capable of forming covalent bonds can include amine-reactive coupling groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Amine-reactive coupling groups can form covalent bonds in a site-specific manner with amines on the analyte. Most of these conjugate to amines by either acylation or alkylation.

Examples of coupling groups can include aldehyde-reactive coupling groups such as hydrazides, alkoxyamines, and primary amines. Aldehyde-reactive coupling groups can form covalent bond in a site-specific manner with aldehyde groups on the analyte.

Examples of coupling groups capable of forming covalent bonds can include sulfhydryl-reactive coupling groups such as maleimide groups, a methanethiosulfonate groups, haloacetyl groups, and pyridyl disulfide groups. Sulfhydryl-reactive coupling groups can form covalent bonds in a site-specific manner with thiol groups on the analyte.

The sulfhydryl-reactive coupling group can be a maleimide group having the formula

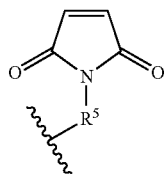

where $R^5$ is a substituted or unsubstituted alkoxy, heteroalkoxy, alkyl, heteroalkyl, aryl, aryloxy, aralkyl, aralkyloxy, alkenyl, or alkynyl group having from 1 to 30, 1 to 20, 1 to 12, or 1 to 6 carbon atoms.

The sulfhydryl-reactive coupling group can be a methanethiosulfonate group having the formula

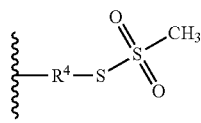

where $R^4$ is a substituted or unsubstituted alkoxy, heteroalkoxy, alkyl, heteroalkyl, aryl, aryloxy, aralkyl, aralkyloxy, alkenyl, or alkynyl group having from 1 to 30, 1 to 20, 1 to 12, or 1 to 6 carbon atoms.

The sulfhydryl-reactive coupling group can be a haloacetyl group having the formula

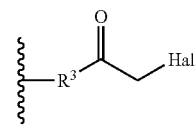

where $R^3$ is a substituted or unsubstituted alkoxy, heteroalkoxy, alkyl, heteroalkyl, aryl, aryloxy, aralkyl, aralkyloxy, alkenyl, and alkynyl groups from 1 to 30, 1 to 20, 1 to 12, or 1 to 6 carbon atoms, and where Hal is a halogen such as Cl, Br, or I.

The sulfhydryl-reactive coupling group can be a pyridyl disulfide group having the formula

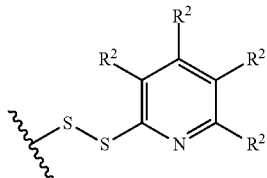

where each occurrence of $R^2$ is independently a hydrogen, hydroxyl, halide, or a substituted or unsubstituted alkoxy, heteroalkoxy, alkyl, heteroalkyl, aryl, aryloxy, aralkyl, aralkyloxy, alkenyl, or alkynyl group having from 1 to 30, 1 to 20, 1 to 12, or 1 to 6 carbon atoms or, when taken together with the atoms to which they are attached form a heterocycle having from 2 to 30, 2 to 20, 3 to 30, 3 to 12, or 6 to 12 carbon atoms.

In other embodiments the site-specific binding is non-covalent, for example a strong non-covalent interaction having a $K_d$ of about $10^{-16}$ M to $10^{-13}$ M, $5 \cdot 10^{-16}$ M to $5 \cdot 10^{-14}$ M, or $10^{-15}$ M to $10^{-14}$ M. hese binding pair members include members of an immunological pair such as antigen-antibody. Non-covalent coupling groups can be avidin, an avidin derivative, streptavidin, a streptavidin derivative, or a combination thereof. Non-covalent coupling groups can include binding pairs such as biotin-avidin (or derivatives thereof such as streptavidin, avidin, or neutravidin), hormones-hormone receptors, IgG-protein A, polynucleotide pairs (e.g., DNA-DNA, DNA-RNA), DNA aptamers. Biotin-avidin/streptavidin pairs are suitable coupling moiety pairs. Biotin (also known as coenzyme R, vitamin H, or vitamin B7) includes the small molecule C10H16N2O3S and derivatives thereof (e.g., ester derivatives between the biotin's carboxylic acid group and a terminal hydroxy group at the 3'-end of the second oligonucleotide) having substantial specific binding affinity to various avidin/streptavidin derivatives. Representative avidin derivatives include the tetrameric protein avidin as well as related derivatives having biotin-binding specificity (e.g., neutravidin as a de-glycosylated form of avidin; recombinant versions of avidin). Representative streptavidin derivatives include the tetrameric protein streptavidin derived from *Streptomyces avidinii* as well as related derivatives having biotin-binding specificity (e.g., recombinant versions of streptavidin; streptavidin derivatives including the biotin-binding regions of streptavidin). The analyte can be an antibody and the coupling group an antigen that binds specifically with the antibody. The analyte can be a polynucleotide and the coupling group an aptamer that binds specifically with an active site of the polynucleotide.

Linker Groups

The DNP agent can include a linker group connecting the coupling group to the poly-radical. The linked group can be a bond, e.g. a single bond or a double bond. The linker group can also be a longer rigid, semi-rigid, or flexible linker. For example the linker group can be a linear or a branched, substituted or unsubstituted alkoxy, heteroalkoxy, alkyl, heteroalkyl, aryl, aryloxy, aralkyl, aralkyloxy, alkenyl, or alkynyl group having from 1 to 30 carbon atoms, 1 to 20 carbon atoms, 1 to 12 carbon atoms, 1 to 10 carbon atoms, 1 to 8 carbon atoms, or 1 to 6 carbon atoms. The linker group can include a carbon chain that can contain heteroatoms (e.g., nitrogen, oxygen, sulfur, etc.) and which may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynyl, amino, alkylamino, azido, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted.

Poly-Radicals

The DNP agent can include a poly-radical, i.e. a molecule or functional group having more than one unpaired electron. The poly-radical can be a di-radical, a tri-radical, or a tetra-radical. The poly-radical can contain 2 or more radicals connected through a flexible or rigid linker, where each radical is independently a nitroxide radical, a triarylmethyl radical, or a combination thereof. For example, each radical can be independently selected for the group 1
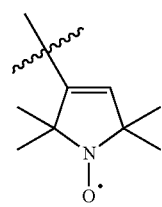

2
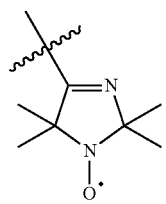

3
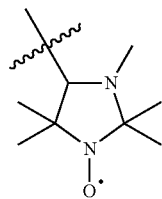

4
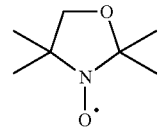

5
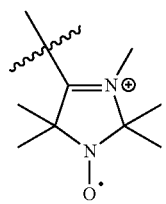

6
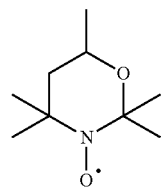

7
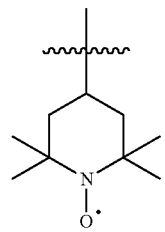

8
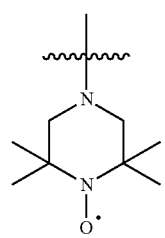

9
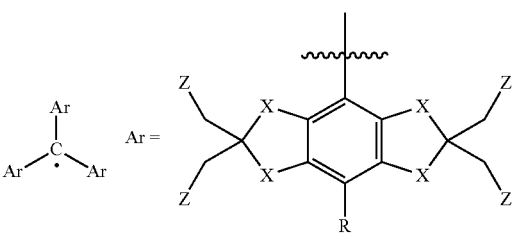

where each occurrence of X is independently $CH_2$, NH, O, or S; and where each occurrence of Z is independently H or a substituted or unsubstituted alkyl, heteroalkyl, alkenyl, or alkynyl group having from 1 to 30, 1 to 20, 1 to 12, 1 to 10, 1 to 8, or 1 to 6 carbon atoms.

The poly-radical can have the formula

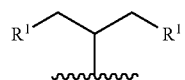

where each occurrence of $R^1$ is independently an $—X^1$-$L^1$-$M^1$; where each occurrence of $X^1$ is —O—, —S—, or —N($R^2$)—, where $R^2$ is H, hydroxyl, halide, or substituted or unsubstituted alkoxy, heteroalkoxy, alkyl, heteroalkyl, aryl, aryloxy, aralkyl, aralkyloxy, alkenyl, and alkynyl groups having from 1 to 30, 1 to 20, 1 to 12, 1 to 10, 1 to 8, or 1 to 6 carbon atoms; where each occurrence of $L^1$ is independently a bond or a substituted or unsubstituted alkoxy, heteroalkoxy, alkyl, heteroalkyl, aryl, aryloxy, aralkyl, aralkyloxy, alkenyl, or alkynyl groups having from 1 to 12, 1 to 6, or 2 to 4 carbon atoms; where each occurrence of $M^1$ is independently a nitroxide radical or a triarylmethyl radical. For example each $M^1$ can be each $M^1$ is independently selected for the group

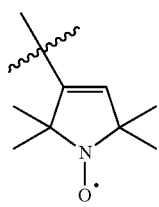
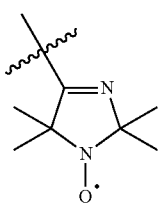
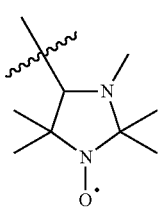
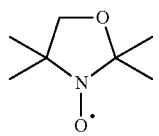
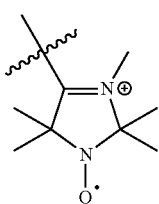
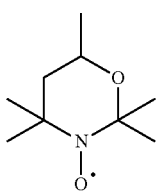
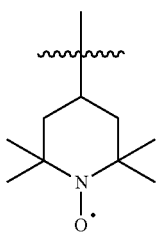

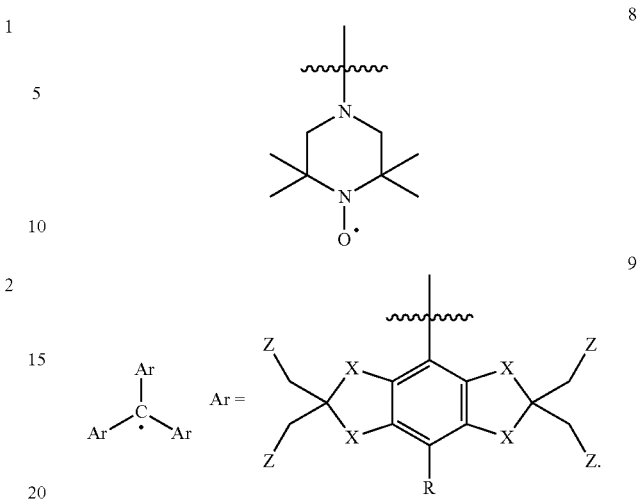

Analytes

The analyte can generally be any molecule that has a site for binding by the coupling group. Suitable sites can include thiols, aldehydes, ketones, amines, and the like. The analyte can be a biomolecule such as a protein or a nucleic acid. In some embodiments the biomolecule is modified to react with the coupling group. The coupling can be through covalent modification of a natural side chain or covalent modification of an unnatural amino acid. The modifications can include modification of the free hydroxyl at the peptide C-terminus using a modification of the mild one-pot esterification method by Hassner and Alexanian (*Tetrahedron Letters*, 1978, 46:4475-4478) as was demonstrated by Dzikovski et al. for spin-labeling of a pentadecapeptide antibiotic gramicidin A (*Biophysical Journal*, 2004, 87(5):3504-3517). The modification can include modification of amino groups a reaction with succinimidyl-2,2,5,5-tetramethyl-3-pyrroline-1-oxyl-3-carboxylate derivatives.

Amphiphilic Groups

The DNP agent can include an amphiphilic group such as an amphiphilic polymer, a lipid, or a conjugate thereof.

Another class of biological systems for DNP NMR involves cellular membranes including model lipid bilayer membranes, liposome preparations, and other mixed lipid-detergent-polymer-protein/peptide systems that are based on self-assembly of surfactant (amphiphilic) molecules. For such systems the DNP agent can be attached (by either covalent bond(s) or strong specific non-covalent interactions such as biotin-streptavidin and/or biotin-avidin) directly to molecule(s) representing an integral part of self-assembled aggregate(s). As an example, we demonstrate an attachment of the biradical DNP agent directly to the polar head group of a phospholipid molecule. Phospholipids represent the major molecular component of cellular membranes that are major structural elements of both prokaryotic and eukaryotic cells. The membranes play a number of roles in biology from defining the cell outer surface and separating various internal compartments to providing specific physicochemical environment for folding and function of membrane proteins. The lipid molecules tailored as the DNP agents could be used in two ways:

a) To enhance NMR signals from other structural components of the self-assembled surfactant layer (i.e., a self-assembled layer formed by amphiphilic molecules) such as lipids, sterols, polysaccharides; and b) To enhance NMR signals from membranes proteins and peptides that are associated with the surfactant layers (i.e., assemblies of amphiphilic molecules). The examples of peptides include antibacterial peptides, attachment and membrane anchoring peptides, signalling peptides, therapeutic peptides including those with cellular targets. The examples of membrane proteins include integral and peripheral membrane proteins. Additional classes involve biomolecules (proteins, peptides, oligoinucleotides, natural and synthetic drug molecules) encapsulated by a surfactant/amphiphile layer (e.g., a liposome) for drug delivery and/or cosmetics purposes.

The amphiphilic group can include an amphiphilic polymer. Amphiphilic polymers can be polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof. In some embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

Hydrophilic polymers include cellulosic polymers such as starch and polysaccharides; hydrophilic polypeptides; poly (amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly (hydroxyalkylmethacrylamide); poly(hydroxyalkylmethacrylate); poly(saccharides); poly(hydroxy acids); poly(vinyl alcohol), and copolymers thereof.

The amphiphilic group can include one or more lipids. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy) propyl]-N,N-dimethyl amine (DODAP), 1,2-diacyloxy-3-dimethylammonium propanes, N-[1-(2,3-dioleyloxy) propyl]-N,N,N-trimethylammonium chloride (DOTMA), 1,2-dialkyloxy-3-dimethylammonium propanes, dioctadecylam idoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), diC$_{14}$-amidine, N-ferf-butyl-N'-tetradecyl-3-tetradecylamino-propionamidine, N-(alpha-trimethylammonio-acetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl) imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Suitable solid lipids include, but are not limited to, higher saturated alcohols, higher fatty acids, sphingolipids, synthetic esters, and mono-, di-, and triglycerides of higher saturated fatty acids. Solid lipids can include aliphatic alcohols having 10-40, preferably 12-30 carbon atoms, such as cetostearyl alcohol. Solid lipids can include higher fatty acids of 10-40, preferably 12-30 carbon atoms, such as stearic acid, palmitic acid, decanoic acid, and behenic acid. Solid lipids can include glycerides, including monoglycerides, diglycerides, and triglycerides, of higher saturated fatty acids having 10-40, preferably 12-30 carbon atoms, such as glyceryl monostearate, glycerol behenate, glycerol palmitostearate, glycerol trilaurate, tricaprin, trilaurin, trimyristin, tripalmitin, tristearin, and hydrogenated castor oil. Suitable solid lipids can include cetyl palmitate, beeswax, or cyclodextrin.

Amphiphilic groups can include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and f-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalm itoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palm itoylglycerophos-phoethanolamine. Synthetic phospholipids with asymmetric acyl chains (e.g., with one acyl chain of 6 carbons and another acyl chain of 12 carbons) may also be used.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Methods of Using DNP Agents

Methods of using the DNP agents are provided. The methods can include MAS NMR methods, allowing for DNP enhancement in a site-specific manner. The methods can also include other standard NMR approaches including liquid NMR approaches and NMR approaches for medical applications. The methods can include dissolution DNP approaches used for MRI.

Methods of NMR measurement of an analyte comprising an NMR-detectable nucleus are provided. The NMR-detectable nucleus can be a half-integer spin nucleus, for example $^1H$, $^{13}C$, $^{15}N$, or $^{19}F$. The analyte can be a protein or a nucleic acid. The methods can include interacting the analyte with a DNP agent provided herein. The DNP agent can react in a site-specific manner with the analyte, for example by forming a covalent bond with a thiol, amine, aldehyde, ketone, or other functional group on the analyte. The DNP agent can react in a site-specific manner with the analyte, for example by forming a non-covalent bond with a site in the analyte, such as a biotinylated site in a protein that interacts with avidin or an avidin derivative. The analyte can be associated with a membrane and the DNP agent can contain an amphiphilic group that non-covalently associates with the membrane.

The methods can include providing a frozen sample containing the analyte and a DNP agent. Optionally, the method can include melting the frozen sample to produce a molten sample prior to detecting the nuclear spin transitions.

The methods can include applying radiation having a frequency that excites electron spin transitions in the DNP agent in an intensity to polarize the NMR-detectable nucleus The methods can include detecting a signal from nuclear spin transitions in the NMR-detectable nucleus. The signal can be greater than a second signal for the otherwise same NMR-detectable nucleus in the same analyte and taken under the same conditions except without the DNP agent in the sample. In some embodiments the signal is at least 2, 3, 4, 5, 10, 100, 500, or even 1,000 times as large as a second signal for the otherwise same NMR-detectable nucleus in the same analyte and taken under the same conditions except without the DNP agent in the sample.

The DNP procedure involves microwave irradiation of the electron paramagnetic resonance (EPR) spectrum of the DNP agent, and results in the transfer of the greater spin polarization of the electrons to the nuclei of surrounding nuclei at or near the site in the analyte. While the methods described herein are not limited to any specific magnetic field and the DNP procedure could be performed at low magnetic fields, the performance of dynamic nuclear polarization (DNP) experiments at the high magnetic fields used in contemporary NMR experiments (e.g., 5-20 T) is preferred.

A high frequency (140-600 GHz), low power (30 mW-3 W) solid state devices and high power (up to 5, 10, 20 W) microwave source can drive the DNP transitions associated with the second order electron-nuclear dipolar interactions in either continuous-wave (CW) or pulsed modes. To date the high power operation has been achieved by utilizing gyrotrons since they operate in the requisite frequency range and produce suitable microwave powers. The relaxation times of the electronic spin systems of radicals and bi- or oligo-radicals dictate that the methods be optimally performed at low temperatures (usually ≤90-120 K). When obtaining high resolution NMR spectra of solids, magic-angle spinning (MAS) is preferably incorporated into the experiment.

When studying molten samples (e.g., by liquid-state NMR), the sample may be recycled by freezing the sample, repolarizing at least one NMR-detectable nucleus of the analyte by irradiating the frozen sample with radiation having a frequency that excites electron spin transitions in the biradical, remelting the frozen sample to produce a molten sample, and redetecting nuclear spin transitions in the at least one NMR-detectable nucleus of the analyte in the molten sample. For example, the sample may be cooled to a temperature in the range of about 1 K to about 100 K. Some of the experiments that are described herein involved cooling the sample to a temperature of about 90 K. In one embodiment, the freezing step may be completed in less than about 2 minutes, e.g., less than about 1 minute.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Experimental Section

Materials and Methods

All chemicals and solvents for the synthesis of ToSMTSL were purchased from VWR International (Radnor, Pa., USA) or Sigma-Aldrich (St. Louis, Mo., USA) unless otherwise indicated, and used without further purification. Common chemicals of a reagent grade for protein expression, isolation and reconstitution were purchased from either Fisher Scientific (Unionville, ON, Canada) or Sigma-Aldrich (Oakville, ON, Canada). The isotopically labeled $^{15}NH_4Cl$ was obtained from Cambridge Isotope Laboratories (Andover, Mass., USA). Lipids were purchased from Avanti Polar Lipids (Alabaster, Ala., USA). The $Ni^{2+}$-NTA (nitrilotriacetic acid) agarose resin was purchased from Qiagen (Mississauga, ON, Canada). Methyl methanethiosulfonate (MMTS) was purchased from Toronto Research Chemicals Inc. (Toronto, ON, Canada).

Sodium methanethiosulfonate was synthesized according to a previously described protocol (Shaked, Z. et al., *Biochemistry* 1980, 19, 4156-4166.) TOTAPOL 3 was synthesized using a slightly modified published procedure (Song, C. S. et al., *J Am Chem Soc* 2006, 128:11385-11390). 4-Methylamino-2,2,6,6-tetramethylpiperdin-1-oxyl 2 was synthesized as described previously (Rosen, G. M., *J Med Chem* 1974, 17:358-360). Crude products were purified on a preparative TLC plate (Kieselgel 60 F254; Merck, Whitehouse, N.J., USA) with mixtures of $CHCl_3$ and $CH_3OH$ as eluents.

Synthesis of Uniformly $^{15}N$ Labeled N148C and S26C Mutants of ASR

[U-$^{15}$N]-labeled (UN), and the natural abundance (NA) C-terminally truncated, His-tagged, N148C and S26C mutants of ASR were produced according to a previously published protocol for wild type (WT) ASR. (Shi, L. et al., *Angew Chem Int Ed Engl* 2011, 50:1302-1305). They are described in the Supporting Information. Proteins were expressed in BL21-Codonplus-RIL *E. coli* grown on M9 minimal medium at 30° C., using 4 g of glucose ($^{13}$C in natural abundance), and 1 g of $^{15}$N-labeled or natural abundance ammonium chloride per liter of culture as the sole carbon and nitrogen sources. When cultures reached a target cell density of $A_{600}$=0.4 OD protein expression was induced by the addition of IPTG to a final concentration of 1 mM and retinal to a final concentration of 7.5 µM. After ~21 hrs the cells were collected by centrifugation, treated with lysozyme (12 mg/L of culture) and DNAase I (600 units per liter of culture) and then broken by sonication. The membrane fraction was then solubilized in 1% DDM (n-dodecyl β-d-maltoside) at 4° C., and purified following the batch procedure described in the Qiagen $Ni^{2+}$-NTA resin manual. Approximately 6 mg of UN N148C and 4 mg of S26C was purified from one liter of culture. The molar amount of the protein was determined from the absorbance of the opsin-bound retinal, using the extinction coefficient of 48,000 $M^{-1}$ $cm^{-1}$. (Wada, Y et al., *Chem Phys Lett* 2008, 453:105-108). Purified proteins were buffer-exchanged using an Amicon Ultra-15 10K centrifugal filter (Millipore, Mass., USA) into reconstitution buffer (5 mM Tris, 10 mM NaCl, 0.05% DDM, pH 8), and concentrated to ~1 mg/ml (36 µM).

Molecular Design and Synthesis of ToSMTSL 1-((1-Oxyl-2,2,6,6-tetramethylpiperidin-4-yl)(methyl)amino)-3-(1-oxyl-2,2,6,6-tetramethylpiperidin-4-yloxy)propan-2-ol 4

Method 1. 2,2,6,6-Tetramethyl-4-(oxiran-2-ylmethoxy)piperidin-1-oxyl 1 (0.17 g, 7.66×10$^{-4}$ mol), 4-methylamino-TEMPO 2 (0.142 g, 7.66×10$^4$ mol), $LiClO_4$ (0.0815 g, 7.66×10$^{-4}$ mol), and 5 mL of $CH_3CN$ were combined in a round-bottomed flask and the reaction mixture was heated on an oil bath at 75° C. under Ar for 48 h while stirring using a magnetic stirrer. When the reaction was completed (as confirmed by TLC), the solvent was removed under reduced pressure, and the residue was purified on a silica gel, using CHCl$_3$+6% v/v CH$_3$OH as an eluent. The fraction with R$_f$=0.3 was collected to yield 4 as a dark red oil, 0.272 g, 85%.

Method 2. TOTAPOL 3 (0.09 g, 2.26×10$^4$ mol) was dissolved in 5 ml of CH$_3$OH containing 0.44 mL (0.0059 mol) of 37% aqueous solution of formaldehyde, and 0.175 mL (0.0041 mol) of 88% formic acid was slowly added to the resulting solution. The reaction mixture was heated at 55-60° C. as the reaction progress was monitored by TLC. After completion of the reaction, the reaction mixture was treated with Et$_3$N until a wet pH indicator paper held over the solution surface showed a basic pH. Consequently, the reaction mixture was concentrated under a reduced pressure and separated on a preparative silica gel TLC plate using CHCl$_3$+6% v/v CH$_3$OH as an eluent. The fraction with R$_f$=0.3 was collected to yield 4 as a dark red oil, 0.082 g, 88%. FT-IR (neat, $\lambda_{max}$, cm$^{-1}$): 3426 (br), 2977, 2935, 2863, 2799, 1466, 1379, 1360, 1242, 1216, 1178, 1110, 751. HRMS (ESI): m/z calcd for C$_{22}$H$_{43}$N$_3$O$_4$, [M+H]: 414.3332. found 414.3317.

1-((1-Oxyl-2,2,6,6-tetramethylpiperidin-4-yl) (methyl)amino)-3-(1-oxyl-2,2,6,6-tetramethylpiperidin-4-yloxy)propan-2-yl 2-bromoethylcarbamate 5

2-Bromoethyl isocyanate (0.073 mL, 8.14×10$^4$ mol) was added to a solution of 4 (0.224 g, 5.42×10$^{-4}$ mol) in 7 mL of EtOAc, and the reaction mixture was allowed to stay at room temperature until completion (monitored by TLC, silica gel, CHCl$_3$+6% v/v CH$_3$OH as eluent). The solvent was removed under reduced pressure and the residue was purified on silica gel using CHCl$_3$+6% v/v CH$_3$OH as eluent. The bromo derivative 5 was obtained as dark red viscous oil, 0.23 g, 74%. FT-IR (neat, $\lambda_{max}$, cm$^{-1}$): 3308 (br), 2973, 2937, 1702, 1523, 1462, 1362, 1245, 1178. HRMS (ESI): m/z calcd for C$_{25}$H$_{47}$BrN$_4$O$_5$ [M+H]: 563.28026. found 563.27995.

O-Methyl 2-((1-((1-oxyl-2,2,6,6-tetramethylpiperidin-4-yl)(methyl)amino)-3-(1-oxyl-2,2,6,6-tetramethylpiperidin-4-yloxy)propan-2-yloxy)carbonylamino)ethanesulfonothioate (ToSMTSL) 6

Sodium methanethiosulfonate dihydrate NaSSO$_2$CH$_3$×2H$_2$O (0.88 g, 0.0052 mol) was added to a solution of bromo derivative 5 (0.21 g, 3.74×10$^4$ mol) in 2 mL of dry DMSO, and the reaction mixture was allowed to stay at room temperature. After the reaction was completed (monitored by TLC, silica gel, CHCl$_3$+6% v/v CH$_3$OH), the reaction mixture was diluted with saline and extracted with EtOAc. An organic extract was thoroughly washed with saline, dried over Na$_2$SO$_3$, and concentrated under a reduced pressure. After a separation on silica gel using CHCl$_3$+6% v/v CH$_3$OH as eluent, the methanethiosulfonate 6 was obtained as red viscous oil, 0.179 g, 86%. FT-IR (neat, $\lambda_{max}$, cm$^{-1}$): 3333 (br), 2973, 2926, 2853, 1716, 1525, 1462, 1362, 1322, 1248, 1179, 1134, 1045, 957, 746, 554. HRMS (ESI): m/z calcd for C$_{26}$H$_{50}$N$_4$O$_7$S$_2$ [M+H]: 595.31937. found 595.31805.

Labeling of ASR with Paramagnetic ToSMTSL and Diamagnetic MMTS and Reconstitution of ASR for DNP Experiments.

Detailed labeling and reconstitution procedures are described below.

Preparation of Diamagnetically Labeled Proteins

The N148C mutant was reacted with methyl methanethiosulfonate (MMTS) (Religa, T. L. et al., *J Am Chem Soc* 2011, 133, 9063-9068) using previously described protocols to yield diamagnetic N148C-S-Met. (Ward, M. E.; et al., *J Biomol NMR* 2014, 58:37-47.) Briefly, solubilized N148C ASR was incubated at room temperature for 1 hr with a 20-fold molar excess of MMTS. Unreacted agent was removed by buffer exchange using an Amicon Ultra-15 10K centrifugal filter. The completeness of spin labelling was monitored and confirmed by HPLC-ESI-Q-TOF Mass Spectrometry.

Spin-Labeling of ASR with ToSMTSL

ToSMTSL was designed as a cysteine-specific biradical molecular probe because of the known high specificity and reactivity of the MTS group to sterically accessible thiol groups. It has been shown previously that the three native cysteine residues C134, C137, and C203 of ASR are not accessible for this reaction. (Wang, S. et al., *J Am Chem Soc* 2012, 134:16995-16998). Two mutant protein strains of ASR, S26C ASR and N148C ASR, were created by introducing additional non-native cysteines at positions 26 and 148, respectively, for paramagnetic labeling. Both mutations are known to not perturb the structure of ASR, and both C26 and C148 are fully accessible to the MTSL labeling.

To label S26C, solubilized S26C ASR (1.1 mL, 1.37 mg/mL, 2.54×10$^{-8}$ mol) in a reconstitution buffer (5 mM NaCl, 10 mM TRIS, 0.05% DDM, pH 8.0) and 33 μL of 8.4 mM stock solution of ToSMTSL (2.77×10$^{-7}$ mol) in acetonitrile were added to a 7.5 ml screw top glass vial, and the resulting solution was briefly vortexed. The tube was then rotated on an Orbitron Rotator (Boekel Scientific, Feasterville, Pa., USA) for ~24 hrs at 4° C. in the dark. After the reaction was complete, the excess spin label was removed by a buffer exchange using an Amicon Ultra-15, 10,000 MWCO centrifugal filter. Briefly, the ASR solution containing the excess label was diluted with the reconstitution buffer to a volume of ~12 ml and then concentrated by centrifugation down to a volume of ~1 ml. The collected buffer solution was discarded and the residual protein solution was diluted with reconstitution buffer up to a volume of ~12 mL. The protein was mixed with the fresh buffer by pulling the solution into the tip of a glass pipette and pushing it back, and the centrifugation/concentration step was repeated. The washing cycles were repeated threefold with the sample being concentrated to the final volume of ~250 μl. The completeness of spin labeling was monitored by HPLC-ESI-Q-TOF Mass Spectrometry. Spectra were taken after ~24 and 30 hrs, and no increase in the spin labeling efficiency was observed between these two time points. The efficiency of labeling of S26C with ToSMTSL was approximately 70-75% as determined by HPLC-ESI-Q-TOF Mass Spectrometry.

To label N148C, solubilized N148C ASR (0.5 mL, 1.49 mg/mL, 2.76×10$^8$ mol) in reconstitution buffer was placed into a 1.5 mL screw-cap microcentrifuge tube (VWR 89004-292), 55 μL of 2.5 mM stock solution of ToSMTSL (1.38×10$^{-7}$ mol) in acetonitrile was added, and the resulting solution was briefly vortexed. The tube was wrapped in an aluminum foil to prevent an accidental exposure of ASR to light, fixed in the clamp of a rotisserie rotator (VWR), and allowed to mix slowly for 48 hrs at room temperature in the dark. After the reaction was complete, the excess spin label was washed out using a centrifuge microconcentration device (Nanosep 10K Omega or VWR 82031-348), 10 k cut-off, 0.5 mL volume. In a typical procedure, 0.5 ml of the ASR solution containing the excess label was placed into the device and concentrated by centrifugation down to the volume of 50-70 μL at a rotation speed not exceeding 8,000 rpm (g=5,900). The collected buffer solution was discarded, the residual protein solution was diluted with the reconstitution buffer up to 0.5 mL volume, layers were carefully mixed by pulling the solution into the tip of a pipette and pushing it back (the pipette tip should always be covered with a solution to prevent bubble formation), and the centrifugation/concentration step was repeated. The washing cycles were repeated until the collected washing solution showed no EPR signal. This was typically achieved after 10 cycles. The efficiency of labeling of N148C was nearly complete as determined by HPLC-ESI-Q-TOF Mass Spectrometry.

Reconstitution of ASR for DNP Experiments

Detergent-solubilized ToSMTSL-labeled ASR (N148C-ToSMTSL and S26C-ToSMTSL in the following) were mixed with diamagnetic N148C-S-Met in the molar ratios specified below. Multilamellar liposomes were prepared by hydrating DMPC:DMPA lipids mixed at a 9:1 ratio (w/w) with a pH 8.0 buffer (5 mM Tris, 10 mM NaCl) and were mixed with the protein solution at 2:1 protein-to-lipid ratio (w/w) and incubated for at least 6 hrs at 4° C. DDM detergent was removed through an addition of Bio-beads (SM-II, Bio-Rad Laboratories, Inc., Hercules, Calif., USA). The protein:lipid ratio of 2:1 (w/w) in the proteoliposomes was confirmed using transmission FTIR spectroscopy (IFS 66 v/S Vacuum FTIR, Bruker Optics, Germany) by comparing the vibration intensities of the lipid esters (at ~1740 $cm^{-1}$) and the protein backbone carbonyls (amide I). (daCosta, C. J.; Baenziger, J. E.: A Rapid Method for Assessing Lipid:Protein and Detergent:Protein Ratios in Membrane-Protein Crystallization. Acta Crystallogr D Biol Crystallogr 2003, 59, 77-83.)

Preparation of ASR Samples for DNP Experiments with TOTAPOL

Purified and solubilized S26C ASR was reconstituted into liposomes as described above for the spin-labelled samples. Lipid-reconstituted S26C ASR was lightly pelleted and resuspended in 0.5 ml of DNP buffer (20 mM TOTAPOL, 60% $d_8$-glycerol, and 40% (w %) NMR buffer (3:1 $D_2O$: $H_2O$, 10 mM NaCl, 24 mM CHES at pH=9). The sample was stirred at 4° C. overnight or until the pellet was completely resuspended. To separate the proteolipsomes from the bulk of the DNP buffer, the sample was centrifuged (900,000×g, 3 hrs, 4° C.); however, it was found that the proteoliposomes were less dense than the 60% $d_8$-glycerol DNP buffer and, therefore, would not pellet. To remedy this, the solution was diluted with the NMR buffer to reduce the $d_8$-glycerol content of the sample to 50%. At this de-glycerol concentration the proteoliposomes could be pelleted under centrifugation, after which they were collected and re-suspended in a fresh 50% $d_8$-glycerol DNP buffer and stirred overnight before being re-pelleted and collected. At this point, additional $d_8$-glycerol was added to the sample to bring the total glycerol content back to approximately 60% (w %). The sample was mixed briefly with a pipette tip in order to uniformly incorporate this additional glycerol before being packed into a 3.2 mm sapphire rotor for MAS DNP-NMR measurements. Based on the amounts of additional de-glycerol and the NMR buffer added, we estimate that the final TOTAPOL concentration of the sample is ~17 mM. Visual inspection of the rotors reveals that this proteoliposome sample occupies approximately 4 times the volume of the same amount of protein without the DNP buffer. This is likely because the increased density of the DNP buffer makes the pelleting of our TOTAPOL sample less efficient.

The number of TOTAPOL molecules per protein monomer was estimated as follows. As the ASR-TOTAPOL sample occupies ~4× the volume of the ASR samples without the glassy matrix components, we can estimate that at least 75% of the volume in ASR-TOTAPOL sample is occupied by DNP buffer. Assuming that DNP buffer accounts for between 75% (lower bound) and 100% (upper bound) of the sample volume of ~15 μl at a TOTAPOL concentration of 17 mM, we estimated the TOTAPOL/monomer ratio to be between 5 and 7.

Continuous-Wave (CW) EPR Experiments

Continuous-wave (CW) EPR spectra of solutions of biradicals and spin-labeled ASR samples were measured with a Varian (Varian Associates, Palo Alto, Calif., USA) Century Series E-102 X-band (9 GHz) spectrometer. Solutions were drawn into a polytetrafluoroethylene tube (PTFE, 0.81×1.12 mm, Jaguar Industries, Stony Point, N.Y.), the tube was folded twice and inserted into a standard X-band 3×4 mm (I.D.×O. D.) quartz EPR tube (Norell, Marion, N.C., USA) for measurements at room temperature. For measurements at 77 K, glycerol was added to a solution at 25 vol % concentration, PTFE tubes were folded a few more times, as many as the diameter of the standard EPR tube would allow, and the tube was inserted into a quartz finger Dewar (Wilmad-LabGlass, Vineland, N.J., USA) filled with liquid nitrogen. Incident microwave power was set below saturation (at 0.06 mW or lower) and the amplitude of the 100 kHz magnetic field modulation was set to a half of the linewidth or less.

Double Electron-Electron Resonance (DEER) Experiments

4-Pulse DEER experiments were performed at X-band (9.5 GHz) using a Bruker ELEXSYS E580 spectrometer (Bruker Biospin, Billerica, Mass., USA). The temperature was stabilized using a Bruker ER 4118CF flow cryostat operated with liquid nitrogen. The liquid sample was pipetted into the standard X-band EPR tube, flash-frozen in liquid nitrogen, and the tube was inserted into a precooled cryostat. The pump and observer frequencies were set at $v_2$=9.632 GHz and $v_1$=9.998 GHz, respectively. For DEER measurements, the acquisition magnetic field was fixed at 3445.0 G, at the maximum of the echo-detected signal at the pump frequency, in order to maximize the fraction of the pumped spins. In order to suppress any unwanted ESEEM contribution, the separation between the first and the second microwave pulses was 136 ns. The separation between the second and the third pulses was 800 ns. The length of the observer pulses were 12 ns and 24 ns for $\pi/2$- and $\pi$-pulses, respectively. The pump pulse of 24 ns length was moved with 2 ns steps over the range of 800 ns.

MAS DNP NMR Experiments

NMR experiments were performed on a 400 MHz/263 GHz Avance III Bruker DNP-NMR spectrometer at the Bruker Biospin facility in Billerica, Mass. A triple resonance (HCN) low temperature MAS DNP probe was used in all of the experiments. The experiments were performed using 3.2 mm sapphire rotors with zirconium caps at a spinning frequency of 8.0 kHz, and at a sample temperature of 102 K, as determined by a calibration using $^{79}$Br Ti measurements in KBr. (Thurber, K. R. et al., *J Magn Reson* 2009, 196:84-87). A 1D $^1$H/$^{15}$N CPMAS experiment was employed to determine the magnitude of the $^1$H DNP enhancements. $^1$H/$^{15}$N cross-polarization was optimized around the n=1 Hartman-Hann condition (Hartmann, S. R, et al., *Phys Rev* 1962, 128: 2042-2053) with 50 kHz r.f. power on $^{15}$N and with the r.f. field linearly ramped around 58 kHz on $^1$H. $^1$H DNP buildup times were estimated using a saturation pulse train applied to the protons, followed by a recovery delay and $^1$H/$^{15}$N CPMAS. Protons were decoupled during $^{15}$N acquisition using 100 kHz SPINAL64 proton decoupling (Fung, B. M. et al., *J Magn Reson* 2000, 142:97-101). DNP enhancements are defined as a ratio $\varepsilon=I_{on}/I_{off}$, where $I_{on}$ and $I_{off}$ are the NMR signal intensities measured with the mm-wave power on and off, respectively.

MM2-Optimized Structure of the Methanethiosulfonate Biradical ToSMTSL

Figure 8:
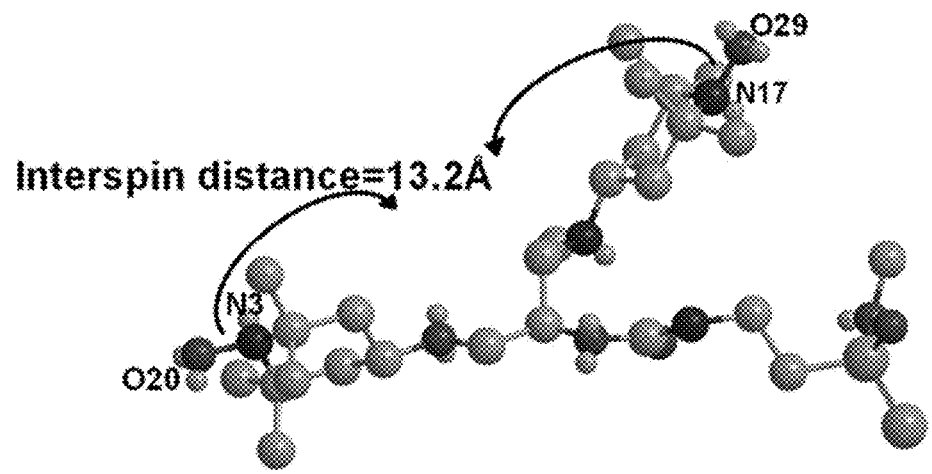
FIG. 8 is a picture of the MM2-optimized structure of the methanethiosulfonate biradical ToSMTSL 6 with the numbering of atoms of the nitroxide groups shown. Hydrogen atoms are omitted for clarity. The interspin distance was defined as a distance between midpoints of the N—O bonds. Assuming that the angle between vectors of the two N—O groups is 136 degree as it was estimated from the optimized geometry of ToSMTSL, the interspin distance was estimated to be 13.2 Å.

The energy minimization and the estimation of the distances between the atoms of the nitroxide moieties in the biradical 6 were carried out using the MM2 method (Chem3D Ultra 9.0 software, CambridgeSoft, Waltham, Mass., USA). The N(3)-N(17) and O(20)-O(29) distances were estimated to be 11.7 Å and 14.0 Å, respectively (FIG. 8).

The following six samples of lipid-reconstituted ASR using either $^{15}$N-labeled or natural abundance N148C and S26C mutants of ASR covalently modified with paramagnetic biradical ToSMTSL (N148C-ToSMTSL, S26C-ToSMTSL) or with diamagnetic methyl methanethiosulfonate (N148C-S-Met) were prepared for DNP experiments (summarized in Table 1):

S1: $^{15}$N-labeled N148C-ToSMTSL reconstituted without diamagnetic dilution; S2: NA N148C-ToSMTSL mixed with $^{15}$N-labeled N148C-S-Met at a 2:1 ratio: S3: $^{15}$N-labeled N148C-S-Met mixed at a 1:1 molar ratio with NA N148C-ToSMTSL; S4: $^{15}$N-labeled N148C-S-Met, NA N148C-S-Met, and NA N148C-ToSMTSL mixed at a molar ratio of 1:2:1; S5: $^{15}$N-labeled S26C-ToSMTSL used without dilution. To prepare the diluted samples S2-S4, diamagnetically and paramagnetically labeled proteins were mixed in the solubilized form prior to reconstitution. It is important to note that the ASR trimers in detergents or lipids do not show any measurable exchange of monomers. This is evident, for example, from the quantitatively similar intermolecular PRE effects measured for the undiluted and diluted samples as reported by us earlier.[45] That is, the diluted sample represents a random mixture of labeled and unlabeled trimers. Each of the samples were prepared in $H_2O$- and $D_2O$-based buffers to evaluate the effect of proton spin diffusion on the distribution of the nuclear spin polarization. In addition, we have prepared a sample containing unmodified S26C with TOTAPOL suspended in the glycerol/$H_2O$/$D_2O$ glassy matrix as explained below (sample S6, Table 1).

Figure 9:
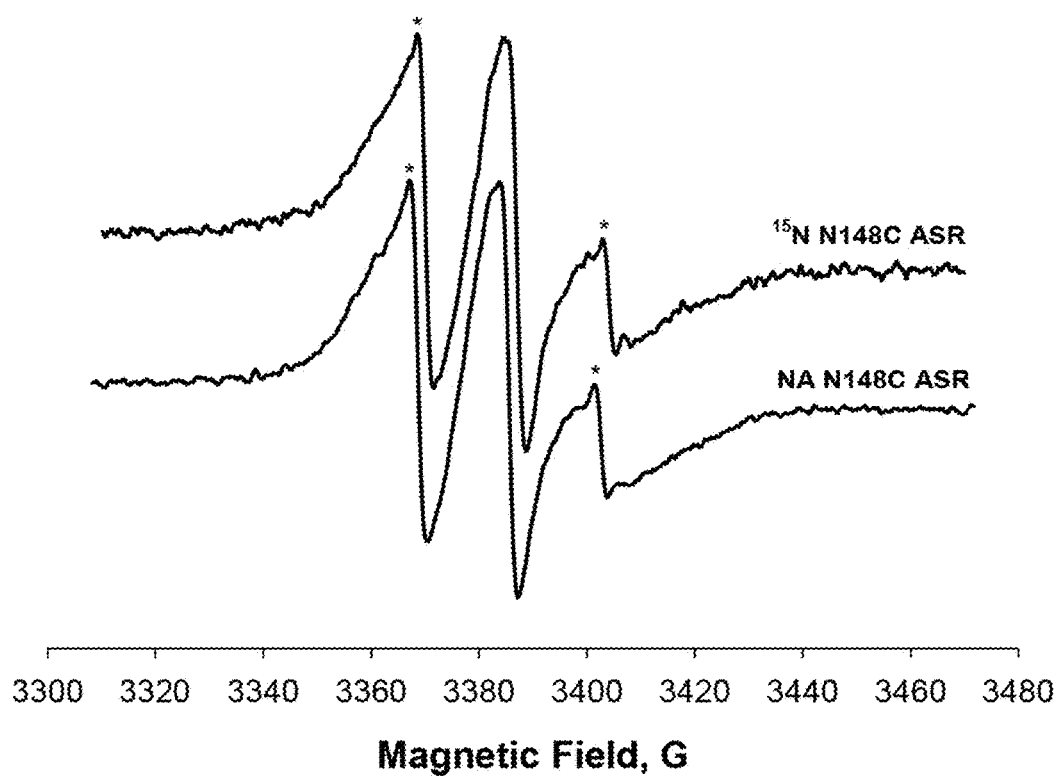
FIG. 9 is a graph of the room temperature X-band (9.5 GHz) EPR spectra of 0.02 mM solution of ToSMTSL-labeled N148C ASR with the natural abundance (NA) of isotopes and of 0.03 mM solution of uniformly $^{15}$N-labeled N148C ASR in a reconstitution buffer (5 mM NaCl, 10 mM TRIS, 0.05% n-decyl-β-D-maltopyranoside (DM), pH=8.0). The nearly identical spectra demonstrate the consistency of the spin-labeling procedure.
Figure 10:
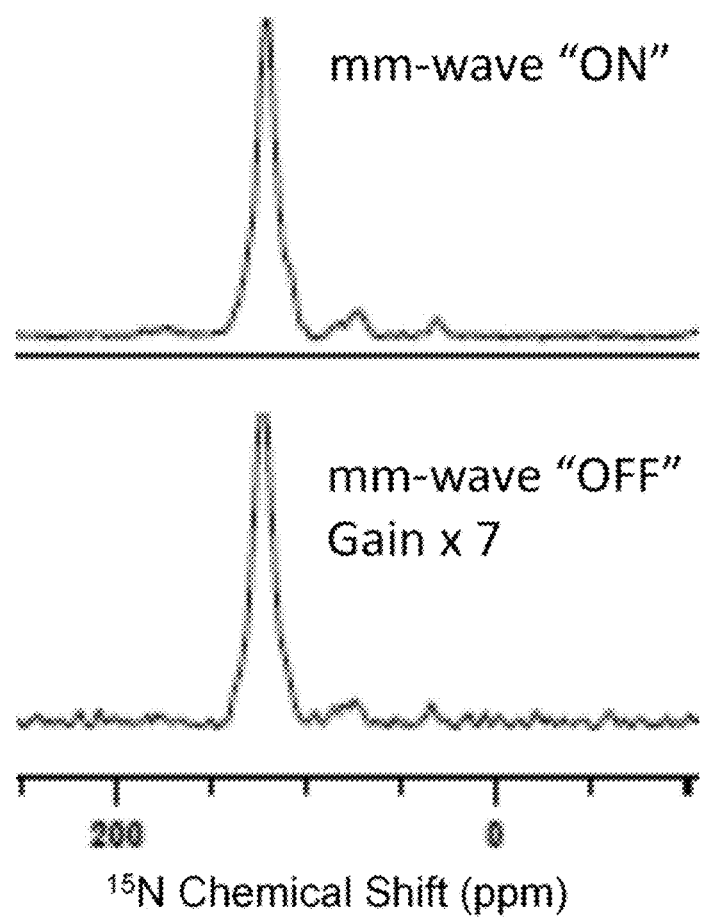
FIG. 10 is an experimental demonstration of how site-specific coupling of the dynamic nuclear polarization (DNP) agent to an immediate surrounding (a phospholipid) of analyte (membrane protein) can lead to signal enhancement in magic angle spinning NMR spectra of the analyte. The graph shows the $^{15}$N CP-MAS NMR spectra from ASR protein imbedded in lipid bilayer structures containing dynamic nuclear polarization (DNP) agent coupled to the lipids. The sample was suspended in a D$_2$O-based buffer and measured on a 400 MHz Bruker Biospin DNP/NMR spectrometer with mm-wave power "ON" (top) and "OFF" (bottom). The vertical scale of the control sample (mm-wave "OFF", bottom) was magnified sevenfold to illustrate $\varepsilon=7$ enhancement. For proper comparison, the cross polarization contact time was the same, and set to 1.4 ms in all the experiments. Spectra were processed with a 200 Hz exponential line broadening.

Room Temperature CW EPR Spectra of the ToSMTSL-Labeled Detergent-Reconstituted N148C Mutant of ASR CW EPR spectra of the ToSMTSL-labeled detergent-reconstituted N148C mutant of ASR solubilized in DDM are shown in FIG. 9. While the three-line pattern originating from the averaging out of the anisotropic $^{14}$N hyperfine tensor dominates the spectral shape, the line shapes are clearly anisotropic, indicating an intermediate motion regime. Such spectra are expected for a nitroxide tag attached through a flexible linker to a loop region of a large, (estimated molecular weight of the ASR-containing DDM micelles is ~600 kDa but freely tumbling protein (Kondo et al., *J Am Chem Soc* 2011, 133:13406-13412). The spectra also contain a minor (<1% of the double-integral intensity) sharp component (shown by the asterisks) that is likely attributed to monoradical impurities resulting from the reduction of a fraction of the biradical 6 with biogenic reducing agents that may be present in the protein preparation in trace quantities. Other possibilities for the origin of the trace signal could be the remaining unreacted label. In either case, the trace signal is not expected to have any measurable effect on the DNP enhancement.

Synthesis of ToSMTSL

We have chosen the biradical TOTAPOL 3—a proven efficient polarization transfer agent for DNP NMR in aqueous solutions[24]—as a scaffold for further chemical modifications. The main objective of our design was to equip this molecule with a tethered thiol-specific methanethiosulfonate functional group, while retaining the electron-electron dipolar coupling of the parent biradical. In order to minimize the amount of acidic protons in the target compound and to reduce the nucleophilicity of the amino group in the original TOTAPOL, an N-methylated derivative of TOTAPOL 4 was synthesized and used as a starting compound for the methanethiosulfonate biradical 6. The derivative 4 was synthesized by two different methods (Scheme 1). In the first method 4-methylamino-2,2,6,6-tetramethylpiperidin 1-oxyl (4-methylamino-TEMPO) 2[46] was N-alkylated with the epoxy derivative 1 similar to the procedure reported for the synthesis of TOTAPOL 3.[24] In the second method TOTAPOL 3 was N-alkylated under conditions of the Esch-

TABLE 1

Sample compositions, bulk $^1$H DNP buildup times, $T_{DNP}$, and the observed DNP enhancement, $\varepsilon$ (defined as a ratio of $^{15}$N NMR signal peak intensities obtained with and without mm-wave irradiation, $\varepsilon = I_{on}/I_{off}$.

| Sample | Sample description[1] | Buffer | $T_{DNP}$ (s) | $\varepsilon$ |
|---|---|---|---|---|
| S1 | $^{15}$N N148C ASR + ToSMTSL (N148C-ToSMTSL) | $H_2O$ | 0.97 ± 0.04 | 9.3 ± 0.4 |
|  |  | $D_2O$ | 0.93 ± 0.03 | 15.0 ± 0.7 |
| S2 | 1:2 $^{15}$N N148C-S-Met:NA-N148C-ToSMTSL | $H_2O$ | 1.14 ± 0.03 | 7.5 ± 0.2 |
|  |  | $D_2O$ | 1.97 ± 0.07 | 9.5 ± 0.7 |
| S3 | 1:1 $^{15}$N N148C-S-Met:NA-N148C-ToSMTSL | $H_2O$ | 0.80 ± 0.04 | 6.4 ± 0.2 |
|  |  | $D_2O$ | 1.55 ± 0.05 | 7.0 ± 0.5 |
| S4 | 1:2:1 $^{15}$N N148C-S-Met:NA-N148C-S-Met:NA-N148C-ToSMTSL | $H_2O$ | 1.74 ± 0.08 | 4.3 ± 0.1 |
|  |  | $D_2O$ | 1.80 ± 0.08 | 4.8 ± 0.4 |
| S5 | $^{15}$N S26C ASR + ToSMTSL (S26C-ToSMTSL) | $D_2O$ | 1.04 ± 0.04 | 11.9 ± 0.5 |
| S6 | $^{15}$N S26C ASR with ~17 mM TOTAPOL | $D_2O$/$H_2O$ glycerol[2] | 0.93 ± 0.03 | 15.2 ± 0.7 |

[1]For the proper comparison of the absolute intensities, each sample contained approximately 1 mg of $^{15}$N labeled protein.
[2]$D_2O$/$H_2O$/$d_8$-glycerol mixed at a ratio of 30/10/60 (w %).
[3]Major contributions to the enhancement error bars are attributed to the uncertainty of evaluation of weak NMR signals with the mm-wave off.

weiler-Clarke reaction (HCOH/HCOOH). Both methods provided the derivative 4 in essentially the same yield of 88%.

flexible linker, which results in a modulation of the electronic spin exchange interaction by an intramolecular motion.[47] The linker flexibility provides for direct collisions Scheme 1. Synthetic route to the methanethiosulfonate biradical spin label ToSMTSL 6. The energy minimized structure of ToSMTSL 6 is shown in FIG. S1.

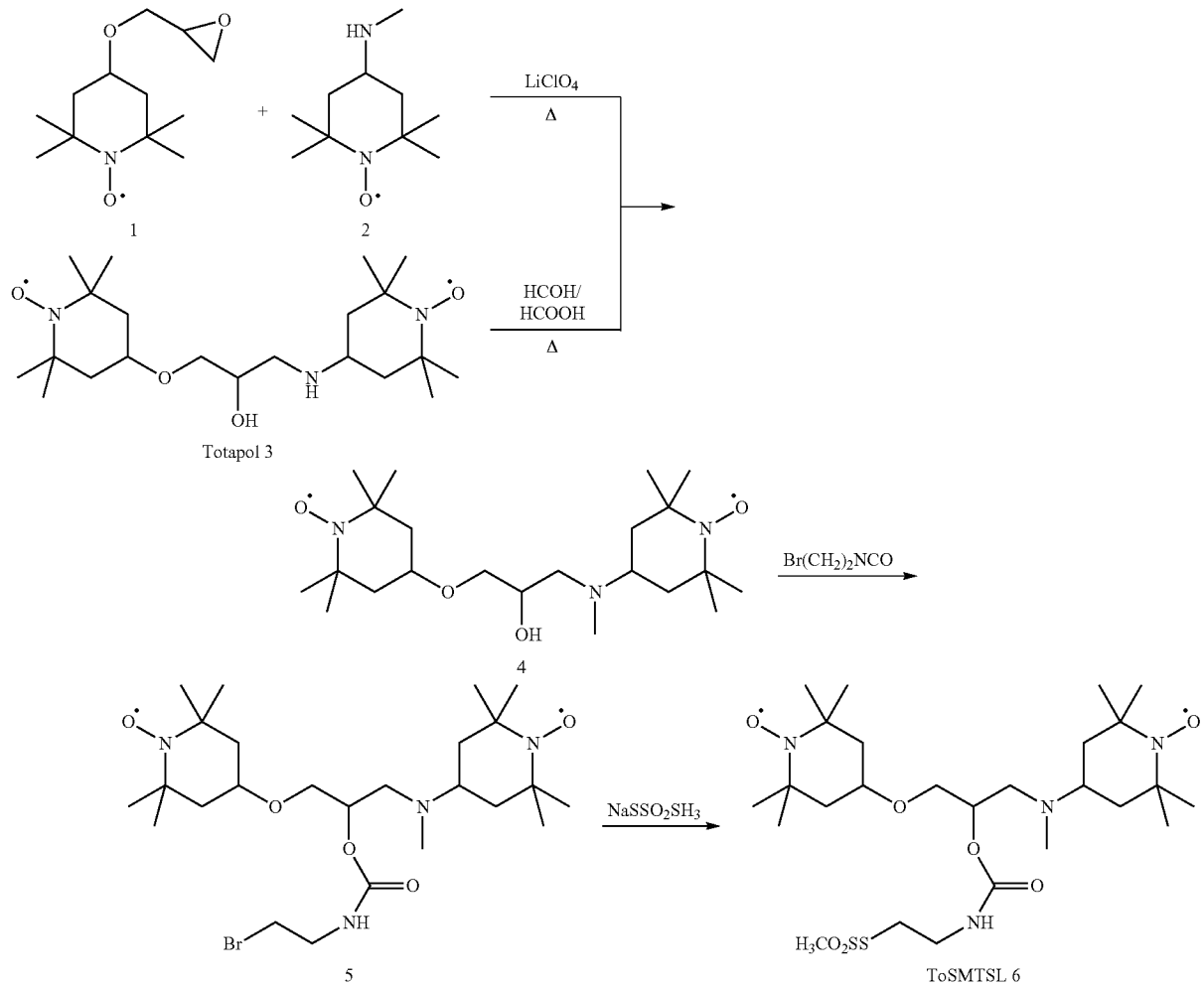

In order to introduce a side chain bearing functionality useful for further transformation into the methanethiosulfonate group, the OH-group in 4 was reacted with 2-bromoethyl isocyanate. This step yielded a rather stable urethane-based tether with a bromide group that is well known to be reactive in the nucleophilic substitution reactions. Thus, the reaction of the bromoethyl derivative 5 with sodium methanethiosulfonate readily afforded the methanethiosulfonate biradical ToSMTSL 6 in a good yield. ToSMTSL is a viscous oil that is readily soluble both in organic solvents such as methanol and acetonitrile, and water.

Characterization of ToSMTSL and ToSMTSL-Labeled ASR by CW EPR

ToSMTSL and ToSMTSL-labeled ASR were characterized by CW EPR at X-band. FIG. 1 compares the room temperature CW X-band (9.5 GHz) EPR spectra of aqueous and i-PrOH solutions of ToSMTSL 6 with those from i-PrOH solutions of the biradical 4 and TOTAPOL 3. All spectra demonstrate a five-line pattern that is typical for the conditions of the fast motion limit for biradicals with a between the N—O• moieties and all the observed spectra are consistent with the average exchange coupling, J, being larger than the nitrogen hyperfine coupling, $A_N$.[48] As expected, the EPR spectrum and magnetic parameters of the biradical 6 are affected by the solvent polarity and viscosity (FIG. 1). For example, replacing water with the less polar and more viscous i-PrOH results in a decrease of the isotropic nitrogen hyperfine coupling constant, $A_{iso}$, from 16.96 G to 16.02 G and in a noticeable line broadening due to slower molecular tumbling of the biradical.

CW EPR spectra of the ToSMTSL-labeled N148C mutant of ASR solubilized in DM (FIG. 9) showed a slower molecular tumbling consistent for a nitroxide tag attached through a flexible linker to a loop region of a large (for a comparison, an estimated molecular weight of the ASR-containing DDM micelles is ~600 kDa[49]) but freely tumbling protein.

Figures 2A, 2B:
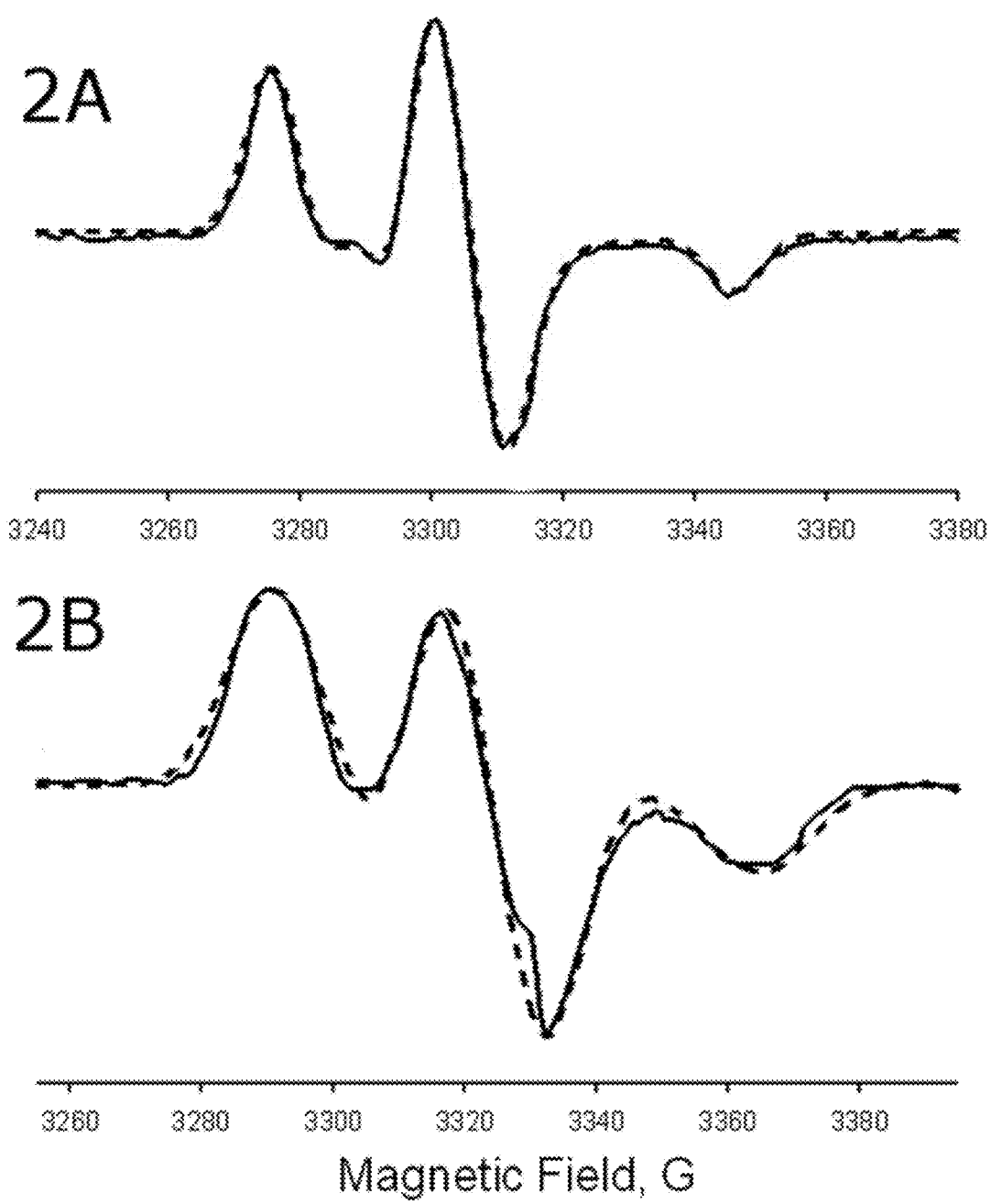
FIGS. 2A-2B are graphs of the experimental rigid limit (T=77 K) X-band (9.5 GHz) EPR spectra (solid lines) of 0.1 mM i-PrOH solution of a monoradical TEMPOL (FIG. 2A) and 1 mM i-PrOH solution the biradical ToSMTSL (FIG. 2B) are superimposed with the best least-squares simulations (dashed lines). The simulations of the biradical spectrum (FIG. 2B) yielded dipolar coupling of $J_{dd}$=25±4 MHz that corresponds to r=12.8±0.8 Å distance between the nitroxide moieties in ToSMTSL.

The rigid limit CW EPR spectrum of a 1 mM i-PrOH solution of the biradical ToSMTSL (FIG. 2B) showed significant inhomogeneous line broadening when compared with a spectrum of a 0.1 mM i-PrOH solution of TEMPOL (4-hydroxy-2,2,6,6-tetramethylpiperidin 1-oxyl) (FIG. 2A), which represents the monoradical fragment of ToSMTSL. This broadening was attributed primarily to intramolecular magnetic electron-electron interactions, mainly the dipolar coupling. The rigid limit EPR spectra were simulated using EasySpin (www.easyspin.org) assuming axially symmetric nitrogen hyperfine coupling tensors ($A_{xx}=A_{yy}$). The best least-squares fits (FIG. 2, red lines) show a close agreement with the experimental spectra (FIG. 2, black lines). Details of the fitting procedure are given in the Supporting Information. The best fit (see Table 2 for the best fit parameters) yielded dipolar coupling of $J_{dd}=25\pm4$ MHz, which compares favourably with the ~23.2 MHz coupling reported for TOTAPOL.[23] The magnitude of $J_{dd}$ allows for estimating $r=12.8\pm0.8$ Å distance between the nitroxide moieties in ToSMTSL. The latter value is in a good agreement with the inter-electron distance of ~13.2 Å obtained from in silico analysis of the molecular structure of the biradical ToSMTSL, assuming that the unpaired electron is localized at the midpoint of the N—O bond of the nitroxides (see FIG. 8).

It should be noted here that the analysis of CW EPR spectra for dipolar broadening is not trivial if the dipolar coupling is not resolved, and could also depend on models of the mutual electronic spin orientations (e.g., see reference [50]), and the presence of monoradical impurities could furthermore complicate this analysis. Thus, we have turned to pulsed EPR methods to characterise the biradical ToSMTSL.

Least-Squares Simulations of Rigid-Limit (77 K) CW X-Band EPR Spectra of i-PrOH Solutions of a Monoradical TEMPOL and a Biradical ToSMTSL The rigid limit EPR spectra were simulated using EasySpin starting with the spectrum of the monoradical and assuming an axially symmetric nitrogen hyperfine coupling tensor ($A_{xx}=A_{yy}$). We note that the dipolar splitting is not resolved in the ToSMTSL rigid limit EPR spectra, whereas the splitting was clearly detected for TOTAPOL in a glassy matrix. The latter could be related to the significant EPR line narrowing obtained by Song and coworkers[1] for $^{15}$N- and $^{2}$H-substituted TOTAPOL, whereas no isotopically substituted ToSMTSL was synthesized yet. The best-fit parameters for the monoradical were used as the starting point for the simulations of the biradical ToSMTSL. The flexibility of the linker was accounted for by a simplified model that involved sampling over 20 homogeneously distributed director orientations on a unit sphere. While the nitroxide rings in ToSMTSL are likely to adapt preferred mutual orientations similar to TOTAPOL, the lack of spectral resolution in X-band EPR spectra from non-isotopically substituted ToSMTSL prevented us from utilizing more accurate fitting models such as a "tether-in-a-cone". (Hustedt et al., Biophys J 2006, 90:340-356) The best fit is shown in FIG. 2B as a black line with the fitting parameters summarized in the Table 2. Note that the dipolar coupling of ~25 MHz is likely an overestimation because the exchange interaction was not accounted for in the simulations, but is also expected to contribute to line broadening the same way the dipolar interaction does.

TABLE 2

Magnetic parameters and inter-electronic spin distance r from least-squares simulations of rigid-limit X-band (9.5 GHz) EPR spectra at 77K of 0.1 mM i-PrOH solution of a monoradical TEMPOL (A) and 1 mM i-PrOH solution a biradical ToSMTSL.

| Sample | $g_{xx}$, $g_{yy}$, $g_{zz}$ | $A_{xx}$,[1] $A_{yy}$,[1] $A_{zz}$, G | Line width,[2] G | Dipolar coupling $J_{dd}$ MHz | Inter-spin distance,[3] r, Å |
|---|---|---|---|---|---|
| Tempol | 2.0100, 2.0068, 2.0025 | 6.8, 6.8, 34.9 | 8.8 | — | — |
| ToSMTSL | 2.0100, 2.0068, 2.0025 | 4.7, 4.7, 38.0 | 11.3 | 25 ± 4 | 12.8 ± 0.8 |
|  | 2.0097, 2.0066, 2.0023 | 7.6, 7.6, 34.5 |  |  |  |

[1]$A_{xx} = A_{yy}$ in the simulations.
[2]Isotropic broadening, measured as the full width at half height of a Gaussian lineshape.
[3]$J_{dd} = 52\,160/r^3$ MHz, (Hu, K. N.; Song, C.; Yu, H. H.; Swager, T. M.; Griffin, R. G.: High-frequency Dynamic Nuclear Polarization Using Biradicals: A Multifrequency EPR Lineshape Analysis. J Chem Phys 2008, 128, 052302.)

Characterization of ToSMTSL and ToSMTSL-Labeled ASR by DEER

One should note that even traces of biogenic reducing agents and/or catalytic metal ions[51,52] in the protein preparation could cause a reduction of one or both nitroxides of the biradical tag. The fraction of the biradical present in the spin-labeled protein was estimated by DEER spectroscopy. The relative magnitude of the modulated component in a DEER trace (i.e., the so-called modulation depth parameter, Δ) is determined by the probability of the microwave excitation of the spin that is spatially correlated to the observed spin, that is, the second spin in the same biradical. Under conditions of an incomplete excitation typical for a DEER experiment, the modulation depth is then given by a product of the spin inversion efficiency, λ, and the fraction, ρ, of the spin pairs present in the sample.[53] Once the parameter λ is determined experimentally for a reference sample with a known fraction of a magnetically identical biradical, the fraction of the biradical in an unknown sample (e.g., a partially reduced biradical in a labeled protein) is estimated by taking the ratio of the modulation depths between the sample and the reference biradical.

While the use of DEER modulation depth for measuring the labeling efficiency (i.e., the fraction of the correlated spin pairs in a sample) is well established,[53] the application of this method to short biradicals such as TOTAPOL and ToSMTSL is not without difficulties related to several factors, including an unaccounted exchange interaction.[53] Typically, the spin exchange is negligible when compared with the dipolar interaction for the distances exceeding 1.5 nm.[54] However, analysis of both the rigid-limit X-band EPR spectra and in silico structures of the biradical 6 yielded the interspin distance of only r=12.8+13.2 Å. The spin exchange was also evident from the extra lines in solution CW EPR of TOTAPOL and ToSMTSL (FIG. 1). Other uncertainties are related to the use of the point dipole approximation for the electronic spins.[53] We note that for such short distance a filtered double-quantum coherence method (DQC)[55] could be applied, but such experiments cannot be carried out with commercial EPR spectrometers.

Figure 3A:
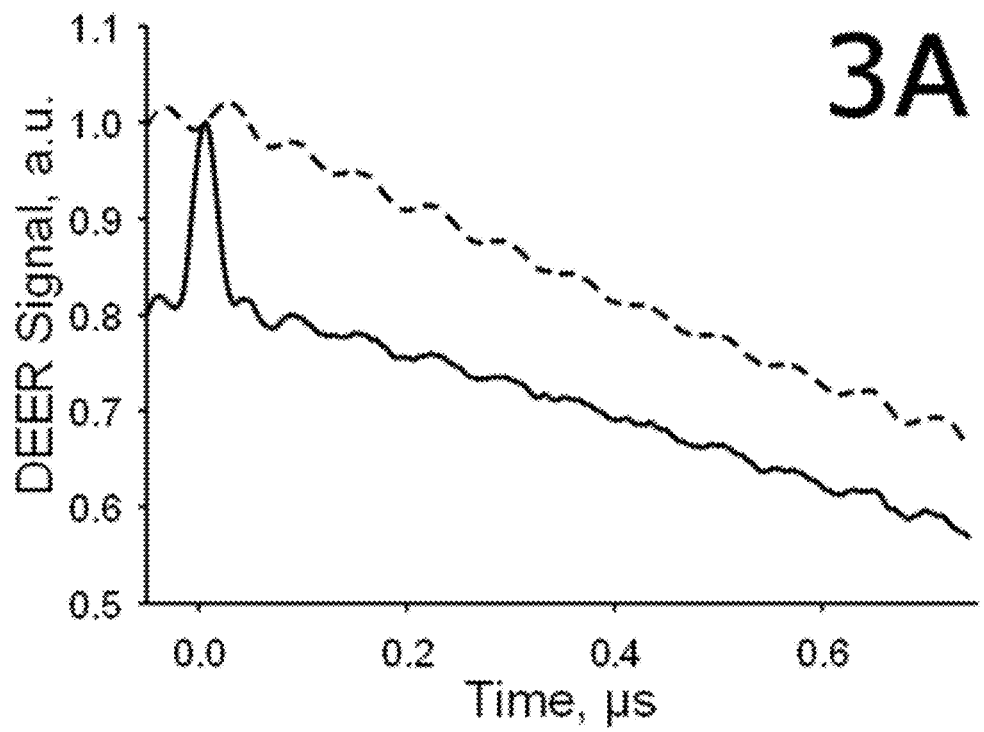
FIG. 3A is a graph of the experimental DEER traces measured at X-band (9.5 GHz) for frozen (T=77 K) i-PrOH solutions of a biradical ToSMTSL (0.5 mM, solid line) and a monoradical 4-amino-TEMPO (1 mM, dashed line)

For the short ca. 12.0-16.0 Å inter-electron distances distortions of the experimental DEER traces at an X-band EPR frequency are simply unavoidable. First, the excitation width of the available microwave pulses is insufficient to cover the entire Pake dipolar pattern of the strongly interacting spins. This leads to a "smoothing" of the DEER modulations and a reduction in the modulation depth.[56] Second, by using 24 ns long π-pulses for both the pump and the observer frequencies separated by 66 MHz, it is impossible to completely avoid unwanted nuclear spin modulations in the DEER traces because the excitation profiles of the pump and the observer pulses partially overlap. Nuclear modulations are caused by electron-nuclear hyperfine interactions and typically appear in single frequency pulsed EPR experiments, where the electron spin echo is measured as a function of the time delay between the pulses. The latter phenomenon is known as an electron spin echo envelope modulation (ESEEM).[57] ESEEM contributions could be effectively suppressed by dividing the DEER trace by a reference trace that is free of the dipolar modulations, but still contains similar ESEEM contributions.[58,59] In order to obtain this reference trace, the DEER signal was measured for a monoradical with the same structure of the heterocycle—4-amino-TEMPO—in a frozen i-PrOH solution at identical experimental conditions (FIG. 3A). The DEER trace of the monoradical contains only the ESEEM modulations and the background decay, i.e., a slow exponential decay due to intermolecular dipolar interactions arising from randomly distributed monoradicals.

Division of the two traces yields an estimate of a "pure" DEER trace, i.e., free of the ESEEM contribution (FIG. 3B) but with some background contributions since the background decay rates are slightly different for the two samples. While for ToSMTSL in the frozen i-PrOH solution the periodic modulations corresponding to the dipolar frequency $v_{AB}$ of 27 MHz were observed (black traces in FIG. 3B), the DEER modulations obtained for the biradical attached to the ASR protein revealed a fast decay without periodic components (blue trace in FIG. 3B). The observed changes in the DEER profile likely originate from a conformational change in the biradical caused by steric effects upon covalent attachment to the protein. The DEER modulation depth, Δ, obtained for the biradical ToSMTSL in i-PrOH, was found to be Δ=0.24. This is lower than the typical modulation depth obtained for rigid biradicals with longer inter-spin distances at a similar microwave excitation bandwidth.[53] The observed reduction in the modulation depth is caused mainly by a significant broadening of the EPR spectrum of the biradical ToSMTSL due to a short interspin distance. An additional reason for the modulation suppression may be the insufficient excitation bandwidth of the microwave pulses to cover the entire Pake pattern of the dipolar interaction (vide supra).

We note here that the trimeric arrangement of ASR solubilized in detergent[45] can bring some of the individual spins of ToSMTSL within the range of intermonomer electronic dipolar interactions. Indeed, an estimate of the inter-spin distances in the N148C trimer yields 49 Å (Cα-Cα distance)[43] which falls within the DEER distance range. Although dipolar interactions within the short biradical are still much stronger and are expected to fully dominate the fast initial drop of the DEER signal, the inter-biradical electronic spin-spin couplings would contribute as a second order effect. While the formation of additional spin pairs is expected to increase the modulation depth of the DEER signal,[53] the latter longer modulations are not fully detected for the short DEER traces acquired and the remaining contributions were effectively filtered out during the background subtraction (FIG. 3).

A comparison of the magnitudes of the DEER modulation yielded the fraction of the biradical ToSMTSL in spin-labeled NA N148C ASR and $^{15}$N-labeled N148C ASR as ~88% and ~89%, respectively. Thus, under our experimental conditions the extent of the biogenic reduction of ToSMTSL upon the ASR labeling was found to be relatively small (~10%). These values should be considered only as an estimate because the effects of the modulation depth suppression due to the insufficient bandwidth of the microwave pulses are difficult to estimate quantitatively for such short distances and such estimates are not the subject of this report. However, we note a potential of DEER measurements for estimating the fraction of the non-reduced biradicals remaining in the labeled protein sample that would be difficult to obtain by mass spectrometry because of a change in the protein weight by just 1 atomic unit.

Figure 3B:
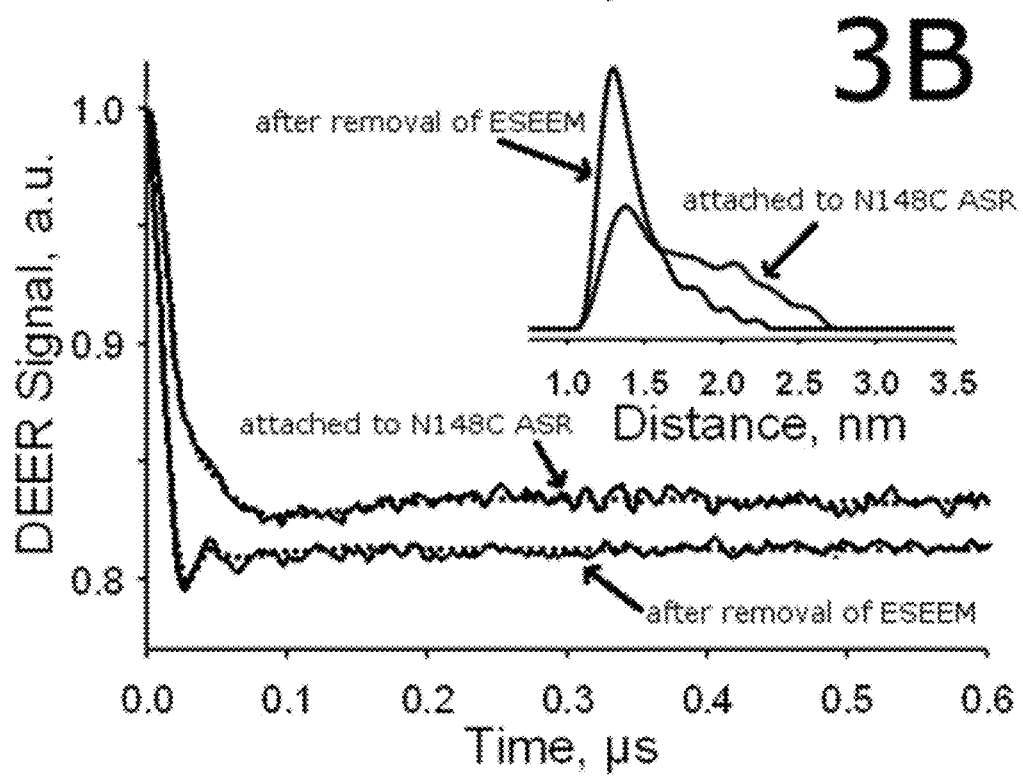
FIG. 3B is a graph of the DEER traces obtained after the removal of ESEEM and the background contributions for the biradical ToSMTSL i-PrOH solution, and when attached to N148C ASR. Simulated DEER traces are shown as dotted lines and the corresponding inter-spin distance distributions are shown as an insert.

Although for short electronic interspin distances the DEER traces cannot be analyzed rigorously, we attempted to estimate changes in the distance distribution upon attachment of ToSMTSL to the protein using the Tikhonov regularization method implemented in the DeerAnalysis2013 software[60] (FIG. 3B insert). The biradical ToSMTSL in i-PrOH shows a relatively narrow distance distribution with a maximum centered at ca. r=13.0 Å (distribution average 14.4±2.3 Å). The maximum of the distance distribution is in excellent agreement with the r=12.8~13.2 Å distances obtained from the analysis of the rigid-limit X-band EPR spectra and in silico structures of ToSMTSL as well as r=13.1±0.6 Å derived from multi-frequency CW EPR experiments for the parent TOTAPOL.[61] For ToSMTSL attached to N148C ASR, the maximum is shifted to ca. r=13.8 Å (distribution average 17.5±4.1 Å). The experimental DEER trace for ToSMTSL attached to $^{15}$N-labeled N148C ASR and the corresponding distance distribution (not shown) were virtually identical to those of the ToSMTSL-N148C ASR sample. This broader distance distribution for ToSMTSL attached to ASR could arise from the remaining unfiltered contributions to the DEER signal from the dipolar interactions between the nitroxides in the individual ASR monomers, and/or unaccounted multispin effects.

DNP NMR Measurements

At low concentrations of biradicals, the cross effect is considered to be the dominant DNP polarization transfer mechanism. It involves one nuclear spin and two electronic spins of the biradical whose Larmor frequencies are separated by the nuclear Larmor frequency. In such a simplified three-spin system the coupled nucleus is polarized as a result of an electronic flip-flop process, and the polarization is further transferred via the interproton spin diffusion to other, more distant protons in the sample. On the one hand, having a biradical close to the protein of interest is beneficial, as it may enhance polarization of the nuclear spins of the protein by both the direct transfer and the interproton spin diffusion. On the other hand, close proximity of the biradical to the protein may induce strong paramagnetic relaxation effects with the associated paramagnetic quenching leading to the signal loss. The electronic spin relaxation time is known to increase at lower temperatures, thus, extending the range of nuclei whose relaxation would be affected by the electronic spins.[62,63] This effect would, however, compete with the expected reduction in the electronic spin relaxation time due to the strong electron-electron dipolar coupling within a biradical, and/or between biradicals in the hexagonal lattice of the ASR trimers.

The knowledge of the placement of the DNP agent allows us to probe in a qualitative manner the effects of the relative biradical concentration and the proximity between the polarizing electronic spins and the nuclear spins of the protein on the electron-nuclear polarization transfer. To probe these effects, we measured DNP enhancements in a series of samples (S1-S6) summarized in the Table 1. We have also investigated the extent of paramagnetic quenching of the NMR resonances and the effect of deuteration of the buffer on the DNP enhancements.

Figure 4:
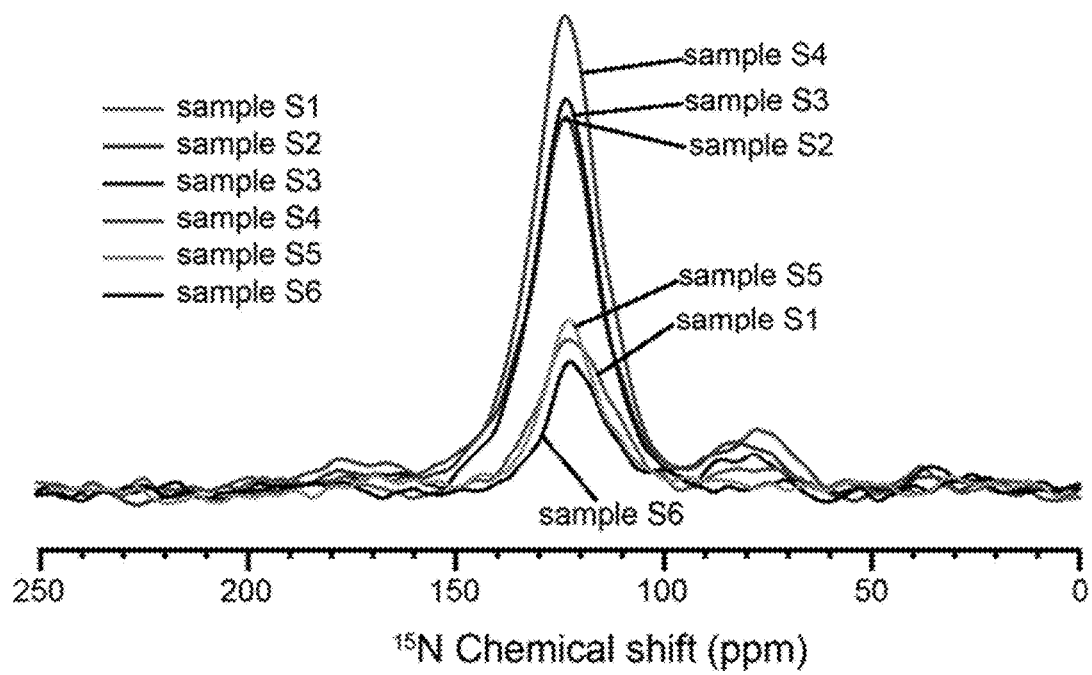
FIG. 4 shows the $^{15}N$ CP-MAS NMR spectra from ASR in an $H_2O$-based buffer, measured on a 400 MHz spectrometer with mm-wave power off. For proper comparison, the cross polarization contact time was the same, and set to 1.4 ms in all the experiments. Spectra were processed with a 200 Hz exponential line broadening.

FIG. 4 shows $^{15}$N CP-MAS NMR spectra of the four N148C samples (S1-S4) and the S26C sample (S5), all covalently labeled with ToSMTSL and reconstituted into lipids using $H_2O$ buffer. As discussed in the Supporting Information, according to mass spectrometry measurements the labeling efficiency of the N148C is nearly 100%, while it is ~70+75% for the S26C. The spectra of S1-S5 samples are compared with the TOTAPOL-doped $^{15}$N ASR prepared in the glycerol/$H_2O$/$D_2O$ matrix (S6), all measured with the mm-wave power off. For convenience of sample preparation we used S26C for the latter sample S6, and this mutation does not affect the protein structure and oligomerization.[45]

The mutated N148 residue in samples S1-S4 is located in the cytoplasmic flank of helix E, and such a location of the biradical label brings the unpaired electrons relatively close, i.e., within ~10-15 Å, to the cytoplasmic face of the protein. Although the exact conformations of the biradical side chain are unknown, it is likely to position the biradical close to helices A and B of the neighbouring monomer within the trimer. As follows from an analysis of the NMR structure of ASR (PDB 2M3G),[43] the intermonomer distances between the Nδ of N148 and some of the atoms in helices A and B are very short, ~10 Å, thus providing efficient paramagnetic quenching pathways. The possible sources of the observed paramagnetic quenching include i) paramagnetic relaxation effect of the electronic spins on (mainly) the transverse relaxation rates and ii) depolarization effect observed in MAS NMR in the presence of a paramagnetic label.[65] Our measurements of the total attenuation do not differentiate between the two contributions and only quantify the total effect.

We note that while $^{15}$N-detected 1D NMR spectra do not provide site specific resolution for this membrane protein oligomer, the data are sufficient to assess the overall effect of the biradical on the NMR signal intensities. Specifically, we observed that the attachment of ToSMTSL to ASR induces a significant, at least ~70% (compared to the most diluted sample), reduction of the signal intensity due to the strong paramagnetic quenching effect.[63] This is generally consistent with the previous observations of the paramagnetic quenching made in the urea sample mixed with TOTAPOL.[66]

Similar signal quenching was observed in another paramagnetically labeled sample S5 (S26C-ToSMTSL), despite a lower, 70-75% efficiency of the ToSMTSL labeling of this mutant, again pointing to the importance of the intermolecular effects within trimers.

The absolute intensities of the signals in the samples S1 and S5 were similar (FIG. 4, small differences may be attributed to slightly different sample amounts) to those observed in the conventionally prepared sample of ASR with TOTAPOL dispersed in the glycerol/water matrix (estimated concentration of TOTAPOL is ~17 mM, or ~6 TOTAPOL molecules per monomer, ~sixfold higher than in the N148C-ToSMTSL sample, and ~ninefold higher than in the incompletely paramagnetically labeled S26C-ToSMTSL sample), suggesting that at least a fraction of TOTAPOL molecules in this conventionally prepared DNP sample are in a close proximity to the protein.

We observe an approximately threefold increase in the NMR signal intensity for the sample S2 in which the $^{15}$N-labeled diamagnetic N148C ASR trimers are mixed in a 1:2 ratio with paramagnetic ASR-ToSMTSL trimers containing $^{15}$N in natural abundance. In such a configuration, the paramagnetic quenching effects in the sample S2 are dominated by the inter-trimer effects. We have shown that the geometry of the ASR trimers (i.e., the overall size, relative orientation of monomers, and the inter-monomer interface) is similar to that of bacteriorhodopsin (BR).[43,45] In lipid bilayers, the trimers form 2D crystals of hexagonal symmetry with a lattice parameter of 66.4 Å.[64] Relative axial orientations of the trimers are unknown. The average C148 Cα-C148 Cα distance within the trimer is ~49 Å.[43] Moreover, hexagonal lattices formed by ASR and BR have similar lattice parameters (66.4 Å for ASR, and 62.7 Å for BR).[64,67] Although the relative axial orientation of the trimers and the inter-trimer interfaces are unknown for ASR, a high similarity to BR is expected due to comparable steric inter-trimer constraints. Based on the analysis of the BR template, we anticipate that C148 would make close inter-trimer contacts to helices E and F, and the biradical can therefore induce a strong quenching in the neighbouring trimer. We see about the same extent of the paramagnetic quenching in sample S3 (FIG. 4), in which every $^{15}$N-labeled trimer interacts, on average, with a paramagnetic neighbour, and a further signal increase in the sample S4, in which a larger fraction of the $^{15}$N-labeled trimers are surrounded by diamagnetic molecules.

Figure 5:
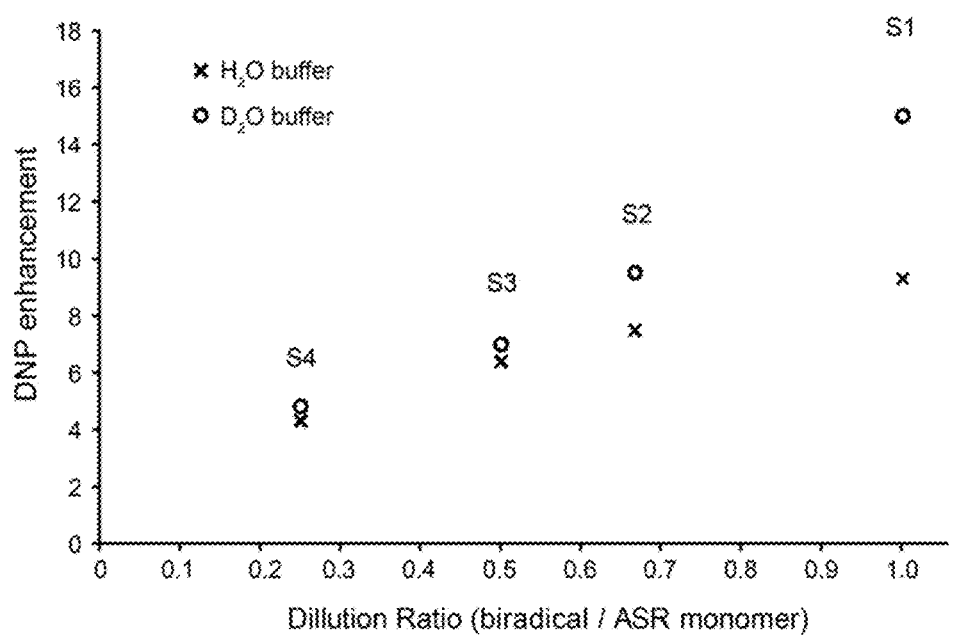
FIG. 5 is a graph comparing the DNP enhancements as a function of paramagnetic dilution for samples S1-S4 prepared in $D_2O$ and $H_2O$ based buffers. To simplify the graph, the error bars are not shown, and are given in the Table 1.

The DNP buildup curves and enhancements were detected using an $^{15}$N CP-MAS experiment under continuous mm-wave irradiation, in which proton spin polarization is initially saturated with a train of 90°-pulses, allowed to build during the recovery delay, and is then detected using $^1H/^{15}N$ CP. Moderate enhancements ranging from ε=4.3 for the most diamagnetically diluted sample S4 to ε=9.3 for the most paramagnetically concentrated sample S1 (biradicals are directly linked to the protein) were obtained, with an apparent increase of the DNP enhancement with the biradical/monomer ratio as shown in FIG. 5. In all the examined samples, we observed relatively short DNP buildup times ($T_{DNP}$) ranging from 0.8 s to ~2.0 s, allowing for accelerated data recording with a recycle delay of 1.3×$T_{DNP}$. Generally, the buildup times are shorter in the samples with a higher concentration of paramagnetic labels, although surprisingly short relaxation rates of 0.8 s and 1.55 s were measured for sample S3, prepared in $H_2O$ and $D_2O$, respectively. Overall, the buildup times compare favourably with the previously reported measurements in BR, where DNP buildup times of 2.6 s were determined for samples prepared with a 20 mM concentration of TOTAPOL measured at a lower temperature of 90 K.[88]

Next, we examined the effect of the available proton bath on the magnitude of the DNP enhancement. Replacement of $H_2O$ with $D_2O$ can affect the DNP enhancement through a reduction of the polarization transferred to the solvent and an increase in the nuclear relaxation time.[69,70] While the presence of deuterium atoms in the solvent tends to attenuate the solvent-mediated spin diffusion process, an efficient spin diffusion pathway through the protons of the lipids, and of the lipid-embedded protein molecules still remains.

Figure 6:
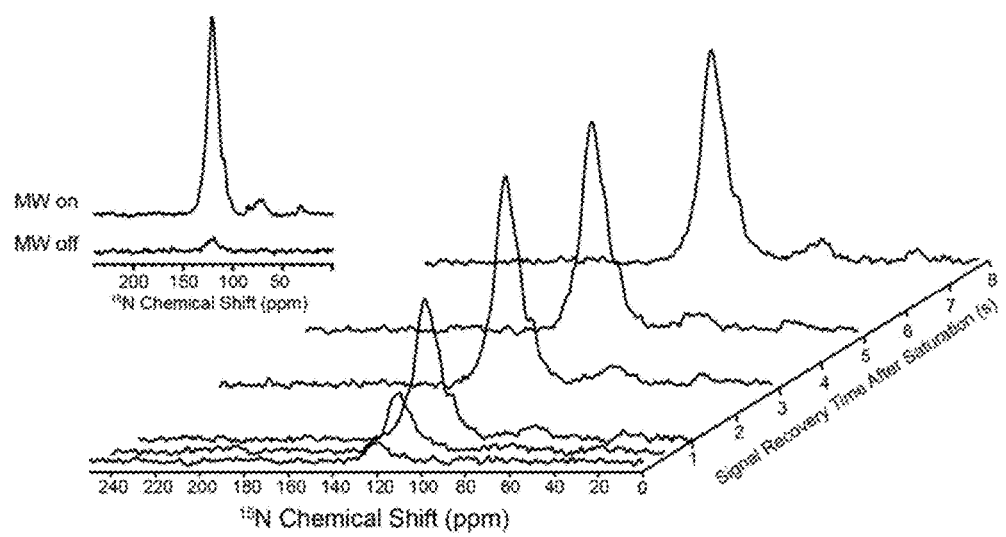
FIG. 6 shows the buildup of the $^{15}$N-detected $^1$H signal following $^1$H signal saturation for $^{15}$N N148C-ToSMTSL measured at 263/400 MHz EPR/NMR frequencies. $^1$H signal buildup time was determined to be 0.93 s in this sample. The inset shows the DNP enhanced spectrum (mm-wave power on) of the same sample compared with the conventional CP-MAS $^{15}$N spectrum (mm-wave power off). The experiment was recorded with a recycle delay of 1.2 s and resulted in an enhancement of $\varepsilon=15$.
Figure 7:
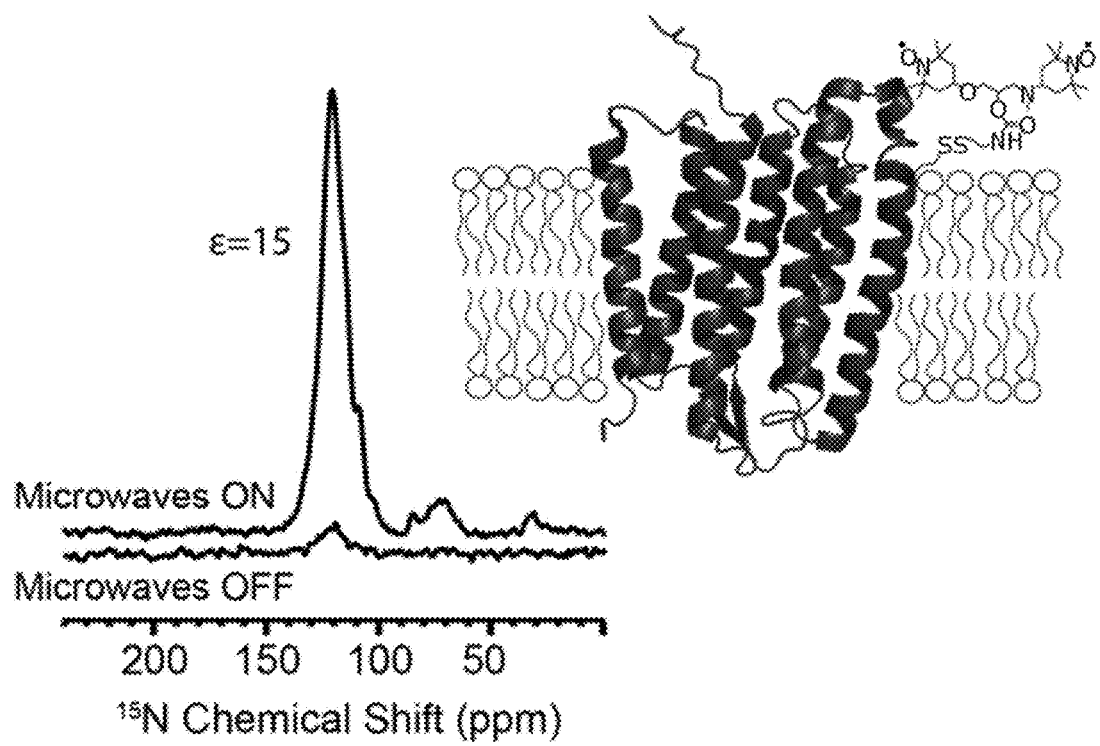
FIG. 7 is a schematic picture demonstrating how site-specific coupling of the dynamic nuclear polarization (DNP) agent to an analyte (protein) can lead to signal enhancement in magic angle spinning NMR spectra of the analyte.

Deuteration has a minimal effect on the DNP buildup rates for the sample S1 (Table 1), but results in longer DNP buildup times for the samples S2-S4, pointing to an increased contribution of spin diffusion for the latter samples. FIG. 6 shows a representative series of Fourier-transformed signals for the sample S1 as a function of the recovery delay, and a comparison between the conventional (mm-wave off) and the DNP-enhanced (mm-wave on) spectra. Specifically, for this sample we observed a DNP buildup time of approximately 1 s and the largest enhancement of ε=15, which is comparable to that observed for ASR-TOTAPOL (sample S6). A slightly lower enhancement of ~12 was observed in S26C-ToSMTSL (sample S5), probably due to an incomplete paramagnetic labeling and a lower biradical/protein ratio.

Summary

In summary, we report on the synthesis of a biradical that can be site-specifically, covalently attached to exposed cysteines, either natively present in a protein or introduced by site-directed mutagenesis. Structurally, this biradical originates from a known DNP polarizing agent TOTAPOL, containing a flexible side chain terminated with thiol-specific methanethiosulfonate functionality. To the best of the authors' knowledge, this is the first demonstration of the use of stable biradicals that can be covalently attached to a protein as polarization agents for DNP.

We demonstrate the utility of this biradical-labeling approach for DNP-enhanced MAS solid state NMR of a lipid-reconstituted heptahelical membrane protein *Anabaena* Sensory Rhodopsin (ASR). We have shown that both the biradical/protein ratio and deuteration of the buffer have strong effects on the DNP enhancements. The largest DNP enhancement of ε=15 was obtained for the sample of ASR directly labeled with ToSMTSL and reconstituted in lipids with a deuterated buffer. This enhancement is comparable with the enhancements obtained under similar experimental conditions for ASR in a $H_2O/D_2O$/glycerol matrix doped with ~17 mM of TOTAPOL. Our approach, however, completely eliminates the limitations related to the solubility of the DNP agents, does not require any glass-forming matrix to achieve a uniform dispersion of the DNP agent, and, for lipid-reconstituted ASR allows for approximately fourfold more protein sample to be packed in the rotor. The latter feature results in improving the absolute sensitivity by a factor of 4 vs. the ASR DNP experiments with TOTAPOL. Furthermore, the relaxed requirement for the glassy matrix would allow for using different cryoprotectants to optimize the solid-state NMR linewidth.[71]

Further improvements in the DNP enhancement can be obtained through optimizing the biradical structural and electronic properties, and by employing partially deuterated lipids.

REFERENCES (1) Mak-Jurkauskas, M. L.; Bajaj, V. S.; Hornstein, M. K.; Belenky, M.; Griffin, R. G.; Herzfeld, J.: Energy Transformations Early in the Bacteriorhodopsin Photocycle Revealed by DNP-Enhanced Solid-state NMR. *Proc Natl Acad Sci USA* 2008, 105, 883-888.

(2) Bajaj, V. S.; Mak-Jurkauskas, M. L.; Belenky, M.; Herzfeld, J.; Griffin, R. G.: Functional and Shunt States of Bacteriorhodopsin Resolved by 250 GHz Dynamic Nuclear Polarization-enhanced Solid-state NMR. *Proc Natl Acad Sci USA* 2009, 106, 9244-9249.

(3) Renault, M.; Pawsey, S.; Bos, M. P.; Koers, E. J.; Nand, D.; Tommassen-van Boxtel, R.; Rosay, M.; Tommassen, J.; Maas, W. E.; Baldus, M.: Solid-state NMR Spectroscopy on Cellular Preparations Enhanced by Dynamic Nuclear Polarization. *Angew Chem Int Ed Engl* 2012, 51, 2998-3001.

(4) Ong, Y. S.; Lakatos, A.; Becker-Baldus, J.; Pos, K. M.; Glaubitz, C.: Detecting Substrates Bound to the Secondary Multidrug Efflux Pump EmrE by DNP-enhanced Solid-state NMR. *J Am Chem Soc* 2013, 135, 15754-15762.

(5) Debelouchina, G. T.; Bayro, M. J.; Fitzpatrick, A. W.; Ladizhansky, V.; Colvin, M. T.; Caporini, M. A.; Jaroniec, C. P.; Bajaj, V. S.; Rosay, M.; Macphee, et al.: Higher Order Amyloid Fibril Structure by MAS NMR and DNP Spectroscopy. *J Am Chem Soc* 2013, 135, 19237-19247.

(6) Fricke, P.; Demers, J. P.; Becker, S.; Lange, A.: Studies on the MxiH Protein in T3SS Needles Using DNP-enhanced ssNMR Spectroscopy. *Chemphyschem* 2014, 15, 57-60.

(7) Kaplan, M.; Cukkemane, A.; van Zundert, G. C. P.; Narasimhan, S.; Daniels, M.; Mance, D.; Waksman, G.; Bonvin, A. M. J. J.; Fronzes, R.; Folkers, et al.: Probing a Cell-Embedded Megadalton Protein Complex by DNP-supported solid-state NMR. *Nat Meth* 2015, 12, 649-652.

(8) Ardenkjaer-Larsen, J. H.; Fridlund, B.; Gram, A.; Hansson, G.; Hansson, L.; Lerche, M. H.; Servin, R.; Thaning, M.; Golman, K.: Increase in Signal-to-noise Ratio of >10,000 Times in Liquid-state NMR. *Proc Nat Acad Sci USA* 2003, 100, 10158-10163.

(9) Golman, K.; in 't Zandt, R.; Thaning, M.: Real-time Metabolic Imaging. *Proc Natl Acad Sci USA* 2006, 103, 11270-11275.

(10) Wilson, D. M.; Hurd, R. E.; Keshari, K.; Van Criekinge, M.; Chen, A. P.; Nelson, S. J.; Vigneron, D. B.; Kurhanewicz, J.: Generation of Hyperpolarized Substrates by Secondary Labeling with [1,1-13C] Acetic Anhydride. *Proc Natl Acad Sci USA* 2009, 106, 5503-5507.

(11) Ross, B. D.; Bhattacharya, P.; Wagner, S.; Tran, T.; Sailasuta, N.: Hyperpolarized MR Imaging: Neurologic Applications of Hyperpolarized Metabolism. *AJNR Am J Neuroradiol* 2010, 31, 24-33.

(12) Lesage, A.; Lelli, M.; Gajan, D.; Caporini, M. A.; Vitzthum, V.; Mieville, P.; Alauzun, J.; Roussey, A.; Thieuleux, C.; Mehdi, A.; et al.: Surface Enhanced NMR Spectroscopy by Dynamic Nuclear Polarization. *J Am Chem Soc* 2010, 132, 15459-15461.

(13) Lelli, M.; Gajan, D.; Lesage, A.; Caporini, M. A.; Vitzthum, V.; Mieville, P.; Heroguel, F.; Rascon, F.; Roussey, A.; Thieuleux, C.; et al.; Fast Characterization of Functionalized Silica Materials by Silicon-29 Surface-enhanced NMR Spectroscopy Using Dynamic Nuclear Polarization. *J Am Chem Soc* 2011, 133, 2104-2107.

(14) Rossini, A. J.; Zagdoun, A.; Lelli, M.; Lesage, A.; Coperet, C.; Emsley, L.: Dynamic Nuclear Polarization Surface Enhanced NMR Spectroscopy. *Accounts of Chemical Research* 2013, 46, 1942-1951.

(15) Takahashi, H.; Viverge, B.; Lee, D.; Rannou, P.; De Paepe, G.: Towards Structure Determination of Self-Assembled Peptides Using Dynamic Nuclear Polarization Enhanced Solid-State NMR Spectroscopy. *Angew Chem Int Ed Engl* 2013, 52, 6979-6982.

(16) Overhauser, A. W.: Polarization of Nuclei in Metals. *Physical Review* 1953, 92, 411-415.

(17) Carver, T. R.; Slichter, C. P.: Polarization of Nuclear Spins in Metals. *Physical Review* 1953, 92, 212-213.

(18) Wind, R. A.; Duijvestijn, M. J.; Vanderlugt, C.; Manenschijn, A.; Vriend, J.: Applications of Dynamic Nuclear-Polarization in C-13 Nmr in Solids. *Progress in Nuclear Magnetic Resonance Spectroscopy* 1985, 17, 33-67.

(19) Maresch, G. G.; Kendrick, R. D.; Yannoni, C. S.; Galvin, M. E.: Dynamic Nuclear-Polarization Via Confined Electrons in Bulk Solids. *Journal of Magnetic Resonance* 1989, 82, 41-50.

(20) Hall, D. A.; Maus, D. C.; Gerfen, G. J.; Inati, S. J.; Becerra, L. R.; Dahlquist, F. W.; Griffin, R. G.: Polarization-enhanced NMR Spectroscopy of Biomolecules in Frozen Solution. *Science* 1997, 276, 930-2.

(21) Hwang, C. F.; Hill, D. A.: New Effect in Dynamic Polarization. *Physical Review Letters* 1967, 18, 110-112.

(22) Hu, K. N.; Debelouchina, G. T.; Smith, A. A.; Griffin, R. G.: Quantum Mechanical Theory of Dynamic Nuclear Polarization in Solid Dielectrics. *J Chem Phys* 2011, 134, 125105.

(23) Hu, K. N.; Yu, H. H.; Swager, T. M.; Griffin, R. G.: Dynamic Nuclear Polarization With Biradicals. *J Am Chem Soc* 2004, 126, 10844-10845.

(24) Song, C. S.; Hu, K. N.; Joo, C. G.; Swager, T. M.; Griffin, R. G.: TOTAPOL: A Biradical Polarizing Agent for Dynamic Nuclear Polarization Experiments in Aqueous Media. *Journal of the American Chemical Society* 2006, 128, 11385-11390.

(25) Matsuki, Y.; Maly, T.; Ouari, O.; Karoui, H.; Le Moigne, F.; Rizzato, E.; Lyubenova, S.; Herzfeld, J.; Prisner, T.; Tordo, P.; et al.: Dynamic Nuclear Polarization with a Rigid Biradical. *Angew Chem Int Ed Engl* 2009, 48, 4996-5000.

(26) Thurber, K. R.; Yau, W. M.; Tycko, R.: Low-temperature Dynamic Nuclear Polarization at 9.4 T with a 30 mW Microwave Source. *Journal of Magnetic Resonance* 2010, 204, 303-313.

(27) Dane, E. L.; Corzilius, B.; Rizzato, E.; Stocker, P.; Maly, T.; Smith, A. A.; Griffin, R. G.; Ouari, O.; Tordo, P.; Swagert, T. M.: Rigid Orthogonal Bis-TEMPO Biradicals with Improved Solubility for Dynamic Nuclear Polarization. *Journal of Organic Chemistry* 2012, 77, 1789-1797.

(28) Sauvee, C.; Rosay, M.; Casano, G.; Aussenac, F.; Weber, R. T.; Ouari, O.; Tordo, P.: Highly Efficient, Water-Soluble Polarizing Agents for Dynamic Nuclear Polarization at High Frequency. *Angew Chem Int Ed Engl* 2013, 52, 10858-10861.

(29) Kiesewetter, M. K.; Corzilius, B.; Smith, A. A.; Griffin, R. G.; Swager, T. M.: Dynamic Nuclear Polarization with a Water-Soluble Rigid Biradical. *J Am Chem Soc* 2012, 134, 4537-4540.

(30) Zagdoun, A.; Casano, G.; Ouari, O.; Lapadula, G.; Rossini, A. J.; Lelli, M.; Baffert, M.; Gajan, D.; Veyre, L.; Maas, et al.: A Slowly Relaxing Rigid Biradical for Efficient Dynamic Nuclear Polarization Surface-enhanced NMR Spectroscopy: Expeditious Characterization of Functional Group Manipulation in Hybrid Materials. *J Am Chem Soc* 2012, 134, 2284-2291.

(31) Zagdoun, A.; Casano, G.; Ouari, O.; Schwarzwalder, M.; Rossini, A. J.; Aussenac, F.; Yulikov, M.; Jeschke, G.; Coperet, C.; Lesage, et al.: Large Molecular Weight Nitroxide Biradicals Providing Efficient Dynamic Nuclear Polarization at Temperatures up to 200 K. *J Am Chem Soc* 2013, 135, 12790-12797.

(32) Yau, W. M.; Thurber, K. R.; Tycko, R.: Synthesis and Evaluation of Nitroxide-Based Oligoradicals for Low-Temperature Dynamic Nuclear Polarization in Solid State NMR. *J Magn Reson* 2014, 244, 98-106.

(33) Koers, E. J.; van der Cruijsen, E. A.; Rosay, M.; Weingarth, M.; Prokofyev, A.; Sauvee, C.; Ouari, O.; van der Zwan, J.; Pongs, O.; Tordo, P.; et al.: NMR-based Structural Biology Enhanced by Dynamic Nuclear Polarization at High Magnetic Field. *J Biomol NMR* 2014, 60, 157-168.

(34) Rossini, A. J.; Zagdoun, A.; Lelli, M.; Gajan, D.; Rascon, F.; Rosay, M.; Maas, W. E.; Coperet, C.; Lesage, A.; Emsley, L.: One Hundred Fold Overall Sensitivity Enhancements for Silicon-29 NMR Spectroscopy of Surfaces By Dynamic Nuclear Polarization with CPMG Acquisition. *Chemical Science* 2012, 3, 108-115.

(35) Takahashi, H.; Lee, D.; Dubois, L.; Bardet, M.; Hediger, S.; De Paepe, G.: Rapid Natural-abundance 2D 13C-13C Correlation Spectroscopy Using Dynamic Nuclear Polarization Enhanced Solid-state NMR and Matrix-free Sample Preparation. *Angew Chem Int Ed Engl* 2012, 51, 11766-11769.

(36) Gajan, D.; Schwarzwalder, M.; Conley, M. P.; Gruning, W. R.; Rossini, A. J.; Zagdoun, A.; Lelli, M.; Yulikov, M.; Jeschke, G.; Sauvee, C.; et al.: Solid-phase Polarization Matrixes for Dynamic Nuclear Polarization from Homogeneously Distributed Radicals in Mesostructured Hybrid Silica Materials. *J Am Chem Soc* 2013, 135, 15459-15466.

(37) Maly, T.; Cui, D.; Griffin, R. G.; Miller, A. F.: 1H Dynamic Nuclear Polarization Based on an Endogenous Radical. *J Phys Chem B* 2012, 116, 7055-7065.

(38) Vitzthum, V.; Borcard, F.; Jannin, S.; Morin, M.; Mieville, P.; Caporini, M. A.; Sienkiewicz, A.; Gerber-Lemaire, S.; Bodenhausen, G.: Fractional Spin-Labeling of Polymers for Enhancing NMR Sensitivity by Solvent-Free Dynamic Nuclear Polarization. *Chemphyschem* 2011, 12, 2929-2932.

(39) Wylie, B. J.; Dzikovski, B. G.; Pawsey, S.; Caporini, M.; Rosay, M.; Freed, J. H.; McDermott, A. E.: Dynamic Nuclear Polarization of Membrane Proteins: Covalently Bound Spin-labels at Protein-Protein Interfaces. *J Biomol NMR* 2015, 61, 361-367.

(40) Takahashi, H.; Ayala, I.; Bardet, M.; De Paepe, G.; Simorre, J. P.; Hediger, S.: Solid-State NMR on Bacterial Cells: Selective Cell Wall Signal Enhancement and Resolution Improvement using Dynamic Nuclear Polarization. *J Am Chem Soc* 2013, 135, 5105-5110.

(41) Smith, A. N.; Caporini, M. A.; Fanucci, G. E.; Long, J. R.: A Method for Dynamic Nuclear Polarization Enhancement of Membrane Proteins. *Angew Chem Int Ed Engl* 2015, 54, 1542-1546.

(42) Fernandez-de-Alba, C.; Takahashi, H.; Richard, A.; Chenavier, Y.; Dubois, L.; Maurel, V.; Lee, D.; Hediger, S.; De Paepe, G.: Matrix-Free DNP-Enhanced NMR Spectroscopy of Liposomes Using a Lipid-Anchored Biradical. *Chemistry* 2015, 21, 4512-4517.

(43) Wang, S.; Munro, R. A.; Shi, L.; Kawamura, I.; Okitsu, T.; Wada, A.; Kim, S. Y.; Jung, K. H.; Brown, L. S.; Ladizhansky, V.: Solid-state NMR spectroscopy Structure Determination of a Lipid-Embedded Heptahelical Membrane Protein. *Nature Methods* 2013, 10, 1007-1012.

(44) Shi, L.; Kawamura, I.; Jung, K. H.; Brown, L. S.; Ladizhansky, V.: Conformation of a Seven-Helical Transmembrane Photosensor In The Lipid Environment. *Angew Chem Int Ed Engl* 2011, 50, 1302-1305.

(45) Wang, S.; Munro, R. A.; Kim, S. Y.; Jung, K. H.; Brown, L. S.; Ladizhansky, V.: Paramagnetic Relaxation Enhancement Reveals Oligomerization Interface of a Membrane Protein. *J Am Chem Soc* 2012, 134, 16995-16998.

(46) Rosen, G. M.: Use of Sodium Cyanoborohydride in Preparation of Biologically-Active Nitroxides. *Journal of Medicinal Chemistry* 1974, 17, 358-360.

(47) Luckhurst, G. R.: In *Spin Labeling: Theory and Applications*; Berliner, L. J., Ed.; Academic Press: New York, 1976; pp 133-181.

(48) Luckhurst, G. R.; Pedulli, G. F.: Interpretation of Biradical Electron Resonance Spectra. *J Am Chem Soc* 1970, 92, 4738-4739.

(49) Kondoh, M.; Inoue, K.; Sasaki, J.; Spudich, J. L.; Terazima, M.: Transient Dissociation of the Transducer Protein from *Anabaena* Sensory Rhodopsin Concomitant with Formation of the M State Produced upon Photoactivation. *J Am Chem Soc* 2011, 133, 13406-13412.

(50) Hustedt, E. J.; Stein, R. A.; Sethaphong, L.; Brandon, S.; Zhou, Z.; DeSensi, S. C.: Dipolar Coupling Between Nitroxide Spin Labels: The Development and Application of a Tether-In-A-Cone Model. *Biophys J* 2006, 90, 340-356.

(51) Beit-Yannai, E.; Zhang, R.; Trembovler, V.; Samuni, A.; Shohami, E.: Cerebroprotective Effect of Stable Nitroxide Radicals in Closed Head Injury in the Rat. *Brain Res* 1996, 717, 22-28.

(52) Zhang, R.; Hirsch, O.; Mohsen, M.; Samuni, A.: Effects of Nitroxide Stable Radicals on Juglone Cytotoxicity. *Arch Biochem Biophys* 1994, 312, 385-391.

(53) Jeschke, G.: DEER Distance Measurements on Proteins. *Ann Rev Phys Chem* 2012, 63, 419-446.

(54) Jeschke, G.: Determination of the Nanostructure of Polymer Materials by Electron Paramagnetic Resonance Spectroscopy. *Macromol Rapid Comm* 2002, 23, 227-246.

(55) Fafarman, A. T.; Borbat, P. P.; Freed, J. H.; Kirshenbaum, K.: Characterizing the Structure and Dynamics of Folded Oligomers: Pulsed ESR Studies of Peptoid Helices. *Chem Commun* 2007, 377-379.

(56) Milov, A. D.; Naumov, B. D.; Tsvetkov, Y. D.: The Effect of Microwave Pulse Duration on the Distance Distribution Function Between Spin Labels Obtained by PELDOR Data Analysis. *Appl Magn Reson* 2004, 26, 587-599.

(57) Dikanov, S. A.; Tsvetkov, Y. D.: *Electron Spin Echo Envelope Modulation ESEEM Spectroscopy* CRC Press: USA, 1992.

(58) Savitsky, A.; Dubinskii, A. A.; Flores, M.; Lubitz, W.; Mobius, K.: Orientation-resolving Pulsed Electron Dipolar High-Field EPR Spectroscopy on Disordered Solids: I. Structure of Spin-Correlated Radical Pairs in Bacterial Photosynthetic Reaction Centers. *J Phys Chem B* 2007, 111, 6245-6262.

(59) Milikisyants, S.; Scarpelli, F.; Finiguerra, M. G.; Ubbink, M.; Huber, M.: A Pulsed EPR Method to Determine Distances Between Paramagnetic Centers with Strong Spectral Anisotropy and Radicals: The Dead-Time Free RIDME Sequence. *J Magn Reson* 2009, 201, 48-56.

(60) Jeschke, G.; Chechik, V.; Ionita, P.; Godt, A.; Zimmermann, H.; Banham, J.; Timmel, C. R.; Hilger, D.; Jung, H.: DeerAnalysis2006—a Comprehensive Software Package for Analyzing Pulsed ELDOR Data. *Appl Magn Reson* 2006, 30, 473-498.

(61) Hu, K. N.; Song, C.; Yu, H. H.; Swager, T. M.; Griffin, R. G.: High-frequency Dynamic Nuclear Polarization using Biradicals: A Multifrequency EPR Lineshape Analysis. *J Chem Phys* 2008, 128, 052302.

(62) Eaton, G. R.; Eaton, S. S.: Frequency Dependence of Electron Spin Relaxation Times. In *Multifrequency Electron Paramagnetic Resonance: Theory and Applications*; Misra, S. K., Ed.; Wiley-VCH, 2011.

(63) Jaroniec, C. P.: Solid-state Nuclear Magnetic Resonance Structural Studies of Proteins using Paramagnetic probes. *Solid State Nucl Magn Reson* 2012, 43-44, 1-13.

(64) Ward, M. E.; Wang, S.; Munro, R. A.; Ritz, E.; Hung, I.; Gor'kov, P. L.; Jiang, Y.; Liang, H.; Brown, L. S.; Ladizhansky, V.: In situ Structural Studies of *Anabaena* Sensory Rhodopsin in the *E. coli* Membrane. *Biophys J* 2015, 108, 1683-1696.

(65) Thurber, K. R.; Tycko, R.: Perturbation of Nuclear Spin Polarizations in Solid State NMR of Nitroxide-Doped Samples by Magic-Angle Spinning without Microwaves. *J Chem Phys* 2014, 140.

(66) Corzilius, B.; Andreas, L. B.; Smith, A. A.; Ni, Q. Z.; Griffin, R. G.: Paramagnet Induced Signal Quenching in MAS-DNP Experiments in Frozen Homogeneous Solutions. *J Magn Reson* 2014, 240, 113-123.

(67) Henderson, R.; Unwin, P. N.: Three-dimensional Model of Purple Membrane Obtained by Electron Microscopy. *Nature* 1975, 257, 28-32.

(68) Barnes, A. B.; Corzilius, B.; Mak-Jurkauskas, M. L.; Andreas, L. B.; Bajaj, V. S.; Matsuki, Y.; Belenky, M. L.; Lugtenburg, J.; Sirigiri, J. R.; Temkin, R. J.; et al.: Resolution and Polarization Distribution in Cryogenic DNP/MAS Experiments. *Phys Chem Chem Phys* 2010, 12, 5861-5867.

(69) Rosay, M.: Sensitivity-enhanced Nuclear Magnetic Resonance of Biological Solids. PhD Thesis, Massachusetts Institute of Technology, 2001.

(70) Akbey, U.; Franks, W. T.; Linden, A.; Lange, S.; Griffin, R. G.; van Rossum, B. J.; Oschkinat, H.: Dynamic Nuclear Polarization of Deuterated Proteins. *Angew Chem Int Ed Engl* 2010, 49, 7803-7806.

(71) Lee, M.; Hong, M.: Cryoprotection of Lipid Membranes for High-Resolution Solid-State NMR Studies of Membrane Peptides and Proteins at Low Temperature. *Journal of Biomolecular Nmr* 2014, 59, 263-277.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A dynamic nuclear polarization (DNP) agent for DNP nuclear magnetic resonance of an analyte, the DNP agent having the structure A-X-L-R, wherein A is an amphiphilic group, wherein X is a coupling group, is selected from the group consisting of an amine-reactive coupling group, an aldehyde-reactive coupling group, a sulfhydryl-reactive coupling group, and a combination thereof, wherein x is capable of site-specific binding with the analyte or with A, wherein L is a bond or a linker group, and wherein R is a poly-radical group, comprising two or more radicals connected through a flexible or rigid linker, where each radical is independently selected from the group consisting of a nitroxide radical, a triarylmethyl radical, and a combination thereof.

2. The DNP agent of claim 1, wherein R is a poly-radical selected from the group consisting of a di-radical, a tri-radical, a tetra-radical, and a combination thereof.

3. The DNP agent of claim 1, wherein each radical is independently selected for the group

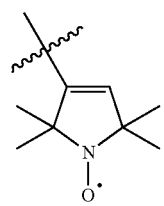

1

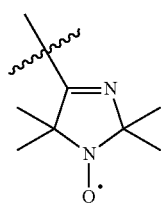

2

-continued

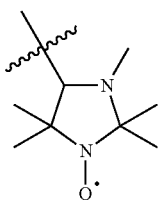
3

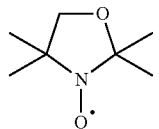
4

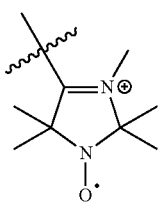
5

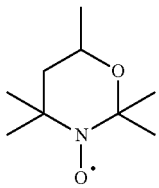
6

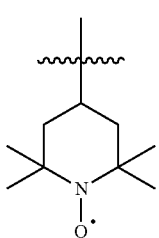
7

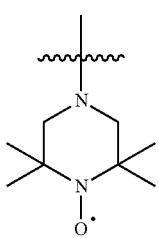
8

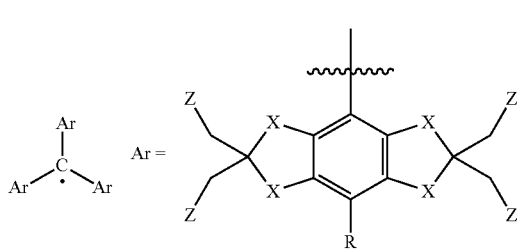
9 wherein each occurrence of X is independently CH$_2$, NH, O, or S;

wherein each occurrence of Z is independently H or a substituted or unsubstituted alkyl, heteroalkyl, alkenyl, or alkynyl group having from 1 to 30 carbon atoms.

4. The DNP agent of claim 1, wherein R has the formula

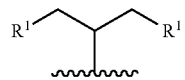

wherein each occurrence of R$^1$ is independently an —X$^1$-L$^1$-M$^1$-;

wherein each occurrence of X$^1$ is selected from the group consisting of —O—, —S—, or —N(R$^2$)—, wherein R$^2$ selected from the group consisting of H, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms wherein each occurrence of L$^1$ is independently a bond or selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 12 carbon atoms;

wherein each occurrence of M$^1$ is independently a nitroxide radical or a triarylmethyl radical.

5. The DNP agent of claim 4, wherein each M$^1$ is independently selected for the group

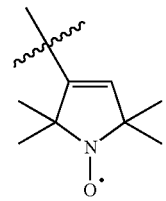
1

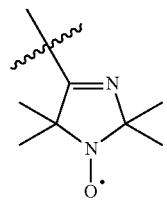
2

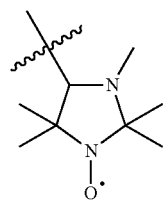
3

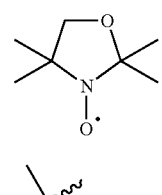
4

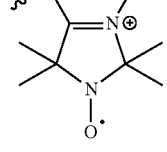
5

6

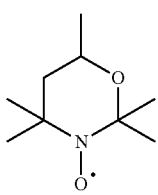

7

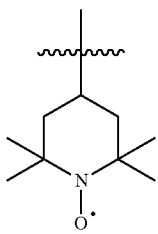

8

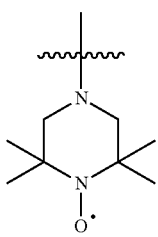

9

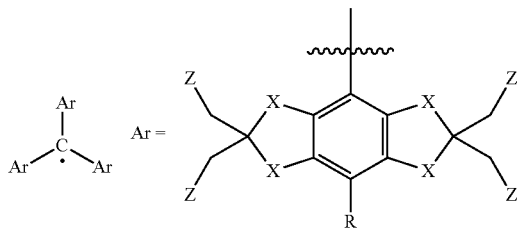

wherein each occurrence of X is independently CH$_2$, NH, O, or S;
wherein each occurrence of Z is independently H or a substituted or unsubstituted alkyl, heteroalkyl, alkenyl, or alkynyl group having from 1 to 30 carbon atoms.

6. The DNP agent of claim 1, wherein the linker group is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 12 carbon atoms.

7. The DNP agent of claim 1, wherein the coupling group forms a covalent bond to the analyte.

8. The DNP agent of claim 1, wherein the coupling group is a sulfhydryl-reactive coupling group selected from the group consisting of a maleimide group, a methanethiosulfonate group, a haloacetyl group, a pyridyl disulfide group, and a combination thereof.

9. The DNP agent of claim 8, wherein the sulfhydryl-reactive coupling group is a maleimide group having the structure

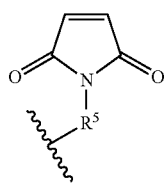

wherein R$^5$ is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms.

10. The DNP agent of claim 8, wherein the sulfhydryl-reactive coupling group is a methanethiosulfonate group having the structure

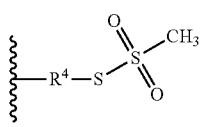

wherein R$^4$ is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms.

11. The DNP agent of claim 8, wherein the sulfhydryl-reactive coupling group is a haloacetyl group having the structure

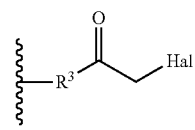

wherein R$^3$ is selected from the group consisting of substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms; and
wherein Hal is a halogen.

12. The DNP agent of claim 8, wherein the sulfhydryl-reactive coupling group is a pyridyl disulfide group having the structure

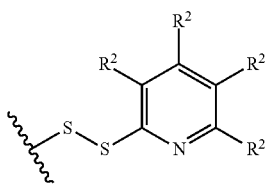

wherein each occurrence of R$^2$ is independently selected from the group consisting of hydrogen, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms or, when taken together with the atoms to which they are attached form a heterocycle having from 2 to 30 carbon atoms.

13. The DNP agent of claim 1, wherein the coupling group is a amine-reactive coupling group selected from the group consisting of an isothiocyanate, an isocyanate, an acyl azide, an NHS ester, a sulfonyl chloride, an aldehyde, an epoxide, an oxirane, a carbonate, an aryl halide, an imidoester, a carbodiimide, an anhydride, a fluorophenyl ester, and a combination thereof.

14. The DNP agent of claim 1, wherein the coupling group is an aldehyde-reactive coupling group selected from the group consisting of a hydrazide, an alkoxyamine, a primary amine, and a combination thereof.

15. The DNP agent of claim 1, wherein the coupling is achieved by click chemistry, including but not limited to coupling between alkyne and azide and by a combination with other coupling schemes.

16. The DNP agent of claim 1, wherein the coupling group is a non-covalent coupling group that binds non-covalently to the analyte with a $K_d$ of $10^{-13}$ M to $10^{-16}$ M.

17. The DNP agent of claim 16, wherein the non-covalent coupling group is selected from the group consisting of biotin, a biotin derivative, avidin, an avidin derivative, streptavidin, a streptavidin derivative, and a combination thereof.

18. The DNP agent of claim 1, wherein the analyte is an antibody and the coupling group is an antigen that binds specifically with the antibody.

19. The DNP agent of claim 1, wherein the analyte is a polynucleotide and the coupling group is an aptamer that binds specifically with an active site of the polynucleotide.

20. The DNP agent of claim 1, wherein A is an amphiphilic group, and wherein the amphiphilic group is selected from the group consisting of an amphiphilic polymer, a lipid, and a conjugate thereof.

21. The DNP agent of claim 1, wherein the analyte is selected from the group consisting of a protein and a nucleic acid.

22. A method of NMR measurement of an analyte comprising an NMR-detectable nucleus, the method comprising the steps of:

providing a frozen sample containing the analyte and a DNP agent according to claim 1;

applying radiation having a frequency that excites electron spin transitions in the DNP agent at an intensity to polarize the NMR-detectable nucleus; and detecting a signal from nuclear spin transitions in the NMR-detectable nucleus.

23. The DNP agent of claim 1, wherein L is a bond.

* * * * *